(12) United States Patent
Tajima et al.

(10) Patent No.: US 9,238,802 B2
(45) Date of Patent: *Jan. 19, 2016

(54) E. COLI TRANSFORMANT, METHOD FOR PRODUCING FLAVIN-BOUND GLUCOSE DEHYDROGENASE USING THE SAME, AND MUTANT FLAVIN-BOUND GLUCOSE DEHYDROGENASES

(75) Inventors: Ryoko Tajima, Noda (JP); Atsushi Ichiyanagi, Noda (JP); Eriko Yoshihara, Noda (JP); Kozo Hirokawa, Noda (JP)

(73) Assignee: KIKKOMAN CORPORATION, Noda-shi, Chiba (JP)

( * ) Notice: Subject to any disclaimer, the term of this patent is extended or adjusted under 35 U.S.C. 154(b) by 237 days.

This patent is subject to a terminal disclaimer.

(21) Appl. No.: 13/991,031

(22) PCT Filed: Nov. 30, 2011

(86) PCT No.: PCT/JP2011/077608
§ 371 (c)(1),
(2), (4) Date: May 31, 2013

(87) PCT Pub. No.: WO2012/073987
PCT Pub. Date: Jun. 7, 2012

(65) Prior Publication Data
US 2013/0309750 A1    Nov. 21, 2013

(30) Foreign Application Priority Data

Dec. 1, 2010 (JP) .................................. 2010-268136
May 9, 2011 (JP) .................................. 2011-103945

(51) Int. Cl.
C12N 9/04    (2006.01)
A61K 38/00    (2006.01)

(52) U.S. Cl.
CPC .................................. *C12N 9/0006* (2013.01)

(58) Field of Classification Search
None
See application file for complete search history.

(56) References Cited

U.S. PATENT DOCUMENTS

| | | | |
|---|---|---|---|
| 7,741,100 B2 * | 6/2010 | Kitabayashi et al. | ...... 435/252.3 |
| 8,445,246 B2 | 5/2013 | Tajima et al. | |
| 9,074,239 B2 | 7/2015 | Tajima et al. | |
| 2006/0063217 A1 | 3/2006 | Omura et al. | |
| 2008/0003628 A1 | 1/2008 | Kitabayashi et al. | |
| 2008/0090278 A1 | 4/2008 | Kitabayashi et al. | |
| 2009/0176262 A1 | 7/2009 | Omura et al. | |
| 2009/0181408 A1 | 7/2009 | Tanaka et al. | |
| 2009/0317848 A1 | 12/2009 | Kawaminami et al. | |
| 2010/0297743 A1 | 11/2010 | Omura et al. | |
| 2010/0323378 A1 | 12/2010 | Honda et al. | |
| 2011/0045513 A1 | 2/2011 | Takenaka et al. | |
| 2011/0053194 A1 | 3/2011 | Yuuki et al. | |
| 2011/0318810 A1 | 12/2011 | Tajima et al. | |
| 2014/0057331 A1 | 2/2014 | Tajima et al. | |

FOREIGN PATENT DOCUMENTS

| | | |
|---|---|---|
| EP | 1862543 A1 | 12/2007 |
| EP | 2241621 A1 | 10/2010 |
| EP | 2508600 A | 10/2010 |
| JP | 2005176602 A | 7/2005 |
| JP | 2007/289148 A | 11/2007 |
| JP | 2008-154574 A | 7/2008 |
| JP | 2008/237210 A | 10/2008 |
| JP | 2010-035448 A | 2/2010 |
| JP | 4494978 B2 | 6/2010 |
| JP | 2010-269056 A | 12/2010 |
| JP | 4648993 B2 | 3/2011 |
| JP | 2011-115156 A | 6/2011 |
| WO | WO 2004/058958 A1 | 7/2004 |
| WO | WO 2006/101239 A1 | 9/2006 |
| WO | WO 2007/139013 A1 | 6/2007 |
| WO | WO 2009/069381 A1 | 6/2009 |
| WO | WO 2009/084616 A1 | 7/2009 |
| WO | WO 2010/140431 A1 | 12/2010 |
| WO | WO 2011/004654 A1 | 1/2011 |
| WO | WO 2011/068050 A1 | 6/2011 |

OTHER PUBLICATIONS

Krasney et al. (1990) "Evolution of the glucose dehydrogenase gene in *Drosophila*", Mol. Biol. Evol., vol. 7, pp. 155-177.*
Glucose dehydrogenase [Flavin] (2005, updated) http://www.uniprot.org/uniprot/P18172, pp. 1-9.*
SEQ-Align (2015) pp. 1-2.*
SEQ-Align II (2015) pp. 1-2.*
SEQ-Align III (2015) pp. 1-2.*
Yamaoka et al., Site Directed Mutagenesis Studies of FAD-dependent Glucose Dehydrogenase Catalytic Subunit of Burkholderia Cepacia, Biotechnol. Lett., Nov. 2008 30(11), pp. 1967-1972.
U.S. Appl. No. 14/355,326, filed Apr. 30, 2014.

(Continued)

*Primary Examiner* — Anand Desai
*Assistant Examiner* — Samuel Liu
(74) *Attorney, Agent, or Firm* — Holtz, Holtz, Goodman & Chick PC

(57) ABSTRACT

A flavin-bound glucose dehydrogenase (FAD-GDH) with high substrate specificity for D-glucose. A gene encoding a mutant FAD-GDH with its N-terminal region, containing an amino acid sequence corresponding to MKITAAIIT-VATAFASFASA that exists in the N-terminal region, deleted from the amino acid sequence of a wild-type FAD-GDH derived from *Mucor* is introduced into *E. coli* to obtain an *E. coli* transformant. Subsequently, this *E. coli* transformant is cultured to obtain an FAD-GDH with a specific N-terminal region deleted. The transformant allows the production of a large amount of GDH in a short time as compared with the original microorganism. An FAD-GDH that is less susceptible to the effects of dissolved oxygen and allows accurate measurement of glucose even in the presence of sugar compounds other than glucose in a sample.

1 Claim, 8 Drawing Sheets

(56) References Cited

OTHER PUBLICATIONS

*Pharmaceuticals and Medical Devices Safety Information*, No. 206 (Oct. 2004) with English translation.

Tchan-Gi Bak et al., "Studies on the Glucose Dehydrogenase *Aspergillus oryzae*", *Biochim. Biophys. Acta*, 139, pp. 256-276 (1967).

Tchan-Gi Bak, "Studies on the Glucose Dehydrogenase *Aspergillus oryzae*", *Biochim. Biophys. Acta*, 139, pp. 277-293 (1967).

Tchan-Gi Bak, "Studies on the Glucose Dehydrogenase *Aspergillus oryzae*", *Biochim. Biophys. Acta*, 139, pp. 317-327 (1967).

Tchan-Gi Bak et al., "Studies on the Glucose Dehydrogenase *Aspergillus oryzae*", *Biochim. Biophys. Acta*, 139, pp. 328-335 (1967).

English-language International Search Report for PCT/JP2011/077608 mailed Mar. 6, 2012.

U.S. Appl. No. 14/124,559, filed Dec. 6, 2013, First Named Inventor: Ryoko Tajima.

U.S. Appl. No. 13/991,087, filed May 31, 2013.

English-language International Preliminary Report on Patentablity and Written Opinion of the International Searching Authority, dated Jun. 13, 2013 for International Application PCT/JP2011/077608 filed Nov. 30, 2011; Applicants: Kikkoman Corporation et al.

Branden, et al., Introduction to Protein Structure, Garland Publishing Inc., New York, p. 247, 1991.

Chica, et al., "Semi-rational approaches to engineering enzyme activity: combining the benefits of directed evolution and rational design", Current Opinion in Biotechnology; Jul. 1, 2005; 16:378-384.

Sen, et al., "Developments in Directed Evolution for Improving Enzyme Functions", Appl Biochem Biotechnol; Aug. 18, 2007; 143:212-223.

\* cited by examiner

Fig. 8

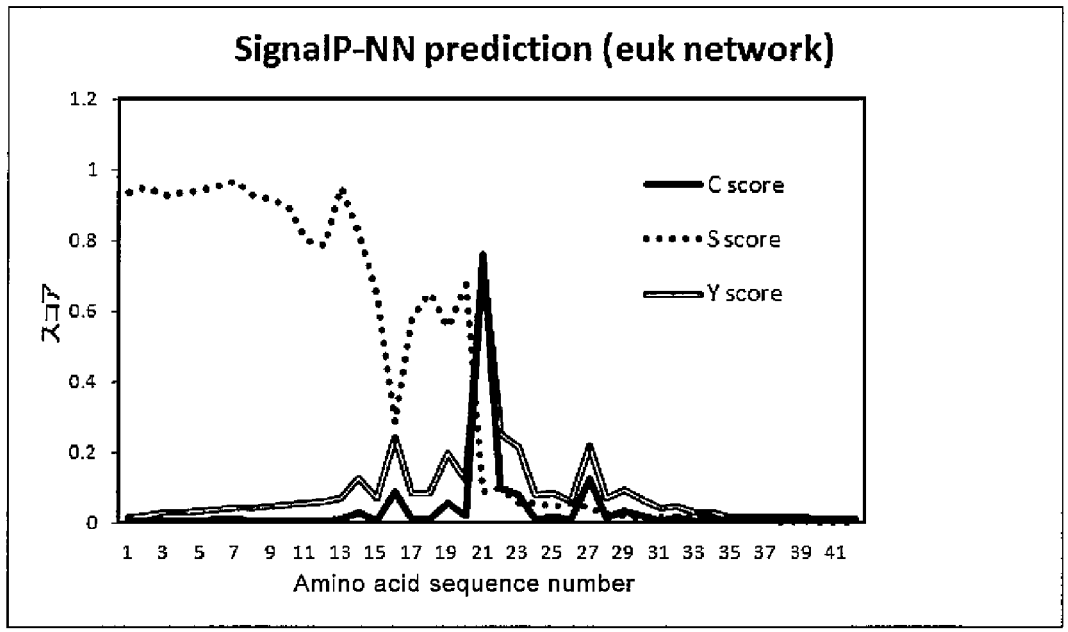

```
>Sequence          length = 42
# Measure  Position  Value   Cutoff  signal peptide?
   max. C    21      0.761   0.32    YES
   max. Y    21      0.734   0.33    YES
   max. S     7      0.967   0.87    YES
   mean S   1-20     0.805   0.48    YES
        D   1-20     0.769   0.43    YES
# Most likely cleavage site between pos. 20 and 21: ASA-QQ
```

Fig. 9

```
MpFull  MKITAAIITVATAFASFASAQQDTNSSSTDTYDYVIVGGGVAGLALASRISENKDVTVAV  60
MpNS1   -----------------MQQDTNSSSTDTYDYVIVGGGVAGLALASRISENKDVTVAV
MpNS2   -----------------MQDTNSSSTDTYDYVIVGGGVAGLALASRISENKDVTVAV
MpNS3   -----------------------MSTDTYDYVIVGGGVAGLALASRISENKDVTVAV
MpNS4   -----------------------MTDTYDYVIVGGGVAGLALASRISENKDVTVAV
```

MpFull: N-terminal region of a full-length GDH containing a signal peptide
MpNS1: N-terminal region of a GDH with a start codon M added to the N-terminal amino acid generated by signal peptide cleavage
MpNS2: N-terminal region of a GDH with the N-terminal amino acid generated by signal peptide cleavage altered to a start codon M
MpNS3: N-terminal region of a GDH with a start codon M added to the 28st Ser
MpNS4: N-terminal region of a GDH with the 28st Ser altered to a start codon M

SEQUENCE LISTING

<160> NUMBER OF SEQ ID NOS: 41

<210> SEQ ID NO 1
<211> LENGTH: 641
<212> TYPE: PRT
<213> ORGANISM: Mucor prainii

<400> SEQUENCE: 1

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
                20                  25                  30

Asp Tyr Val Thr Val Gly Gly Gly Val Ala Gly Leu Ala Leu Ala Ser
            35                  40                  45

Arg Ile Ser Glu Asn Lys Asp Val Thr Val Ala Val Leu Glu Ser Gly
    50                  55                  60

Pro Asn Ala Asn Asp Arg Phe Val Val Tyr Ala Pro Gly Met Tyr Gly
65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
                100                 105                 110

Gly Gly Gly Ser Ala Ile Asn Gly Leu Val Trp Thr Arg Gly Gly Leu
            115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
    275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
                340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Tyr Ala Ser Thr Asn Ala Ser
                420                 425                 430

Asn Val Glu Leu Leu Lys Lys Gln Tyr Ala Ile Val Ala Ser Arg Tyr
            435                 440                 445

Glu Glu Asn Tyr Leu Ser Pro Ile Glu Ile Asn Phe Thr Pro Gly Tyr
    450                 455                 460

Glu Gly Ser Gly Asn Val Asp Leu Gln Asn Asn Lys Tyr Gln Thr Val
465                 470                 475                 480

Asn His Val Leu Ile Ala Pro Leu Ser Arg Gly Tyr Thr His Ile Asn
                485                 490                 495

Ser Ser Asp Val Glu Asp His Ser Val Ile Asn Pro Gln Tyr Tyr Ser
                500                 505                 510

His Pro Met Asp Ile Asp Val His Ile Ala Ser Thr Lys Leu Ala Arg
    515                 520                 525

Glu Ile Ile Thr Ala Ser Pro Gly Leu Gly Asp Ile Asn Ser Gly Glu
    530                 535                 540

Ile Glu Pro Gly Met Asn Ile Thr Ser Glu Asp Asp Leu Arg Ser Trp
545                 550                 555                 560

Leu Ser Asn Asn Val Arg Ser Asp Trp His Pro Val Gly Thr Cys Ala
                565                 570                 575

Met Leu Pro Lys Glu Leu Gly Gly Val Val Ser Pro Ala Leu Met Val
                580                 585                 590

Tyr Gly Thr Ser Asn Leu Arg Val Val Asp Ala Ser Ile Met Pro Leu
    595                 600                 605

Glu Val Ser Ser His Leu Met Gln Pro Thr Tyr Gly Ile Ala Glu Lys
    610                 615                 620

Ala Ala Asp Ile Ile Lys Asn Phe Tyr Lys Thr Gln His Lys Asn Gln
625                 630                 635                 640

Asn

<210> SEQ ID NO 2
<211> LENGTH: 1926
<212> TYPE: DNA
<213> ORGANISM: Mucor prainii

<400> SEQUENCE: 2

```
atgaagatca cagctgccat tatcactgtt gccacagcat ttgcttcttt tgcttctgct    60
caacaagaca caaattcttc ctcaactgat acttatgatt atgttaccgt tggcggcggt   120
gtagctggtt tggctttggc tagtcgtatc tctgaaaaca aggatgtcac tgttgctgtt   180
ctcgagtccg gtcctaatgc caatgataga tttgttgttt atgctcctgg catgtatggc   240
caagctgttg cactgatct ctgtcctctc attcctacta ctcctcaaga aaatatgggc   300
aacagaagtc tcacaatcgc tactggtaga ttgctcggtg gtggcagtgc tattaatggt   360
ctcgtttgga cccgtggtgg cttgaaggat tacgatgctt gggaggagct cggtaaccct   420
ggatggaacg tgccaacttt gttcaagtac tttaagaagg tcgaaaactt cactcctcct   480
actcctgcac aaattgaata cggcgctact tatcagaaaa gtgctcatgg caagaaggga   540
cctattgatg tctcttttcac gaactacgag ttctctcaat ctgctagctg aacgcctca   600
ctcgaaaccc ttgatttcac tgcacttcct gatatcttga acggtacttt ggccggttac   660
tctaccactc ccaacatttt ggaccctgag actgttcaac gtgttgattc ctatactggt   720
tacattgctc cttacactag ccgtaacaac ctcaatgttt tggccaacca taccgtctcc   780
cgcattcaat ttgctcccaa gaatggtagc gaacctctca aggctaccgg tgttgaatgg   840
tatcccactg gcaacaagaa tcaaaagcaa attatcaagg cccgttatga agttatcatc   900
tcatctggtg ccattggtag tcctaagctt ttggaaatct ctggtatcgg taataaggat   960
atcgtctctg ctgctggtgt cgagtccttg attgacttgc ctggcgttgg ttccaacatg  1020
caagatcacg ttcatgctat cactgtctct actaccaata ttactggcta tactaccaac  1080
agcgtctttg tcaatgaaac ccttgcccaa gaacaaagag aagaatatga agccaacaag  1140
actggtatct gggctactac tcccaacaac ctcggttatc ctacgcccga caactcttc   1200
aatggcaccg aattcgtttc tggaaaggag tttgctgaca gattcgtaa ctctactgat   1260
gaatgggcca actattatgc ttccaccaac gcctccaatg tcgagttatt aaagaagcaa  1320
tatgctattg tcgcctctcg ttacgaagag aactacttgt ctcctattga aatcaacttc  1380
actcctggtt atgagggtag cggtaatgtc gatttgcaaa caacaagta ccaaactgtc   1440
aaccatgtct tgattgctcc tttaagtcgt ggttatactc acattaactc ttctgatgtg  1500
gaggatcatt ctgtcattaa tccccaatac tactctcatc ctatggatat tgatgtccat  1560
atcgcttcca ctaaacttgc tcgcgaaatc atcactgcct ctcccggtct tggtgacatt  1620
aacagtggcg aaatcgaacc cggtatgaat attacttctg aagacgacct tagatcttgg  1680
ttgagtaata atgtccgttc tgactggcat cctgttggta cttgtgctat gcttcccaag  1740
gaattaggtg gtgttgtcag ccccgctctc atggtttacg gcacttccaa cttgcgtgtt  1800
gttgatgctt cgattatgcc cctcgaagtc tcttctcatt tgatgcaacc cacctacggt  1860
attgctgaga aggctgctga cattattaag aatttctaca agactcaaca caagaaccaa  1920
aattag                                                             1926
```

<210> SEQ ID NO 3
<211> LENGTH: 641
<212> TYPE: PRT
<213> ORGANISM: Mucor prainii

<400> SEQUENCE: 3

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr

```
                20                  25                  30
Asp Tyr Val Ile Val Gly Gly Val Ala Gly Leu Ala Leu Ala Ser
            35                  40                  45

Arg Ile Ser Glu Asn Lys Asp Val Thr Val Ala Val Leu Glu Ser Gly
 50                  55                  60

Pro Asn Ala Asn Asp Arg Phe Val Val Tyr Ala Pro Gly Met Tyr Gly
 65                  70                  75                  80

Gln Ala Val Gly Thr Asp Leu Cys Pro Leu Ile Pro Thr Thr Pro Gln
                85                  90                  95

Glu Asn Met Gly Asn Arg Ser Leu Thr Ile Ala Thr Gly Arg Leu Leu
            100                 105                 110

Gly Gly Gly Ser Ala Ile Asn Gly Leu Val Trp Thr Arg Gly Gly Leu
        115                 120                 125

Lys Asp Tyr Asp Ala Trp Glu Glu Leu Gly Asn Pro Gly Trp Asn Gly
    130                 135                 140

Ala Asn Leu Phe Lys Tyr Phe Lys Lys Val Glu Asn Phe Thr Pro Pro
145                 150                 155                 160

Thr Pro Ala Gln Ile Glu Tyr Gly Ala Thr Tyr Gln Lys Ser Ala His
                165                 170                 175

Gly Lys Lys Gly Pro Ile Asp Val Ser Phe Thr Asn Tyr Glu Phe Ser
            180                 185                 190

Gln Ser Ala Ser Trp Asn Ala Ser Leu Glu Thr Leu Asp Phe Thr Ala
        195                 200                 205

Leu Pro Asp Ile Leu Asn Gly Thr Leu Ala Gly Tyr Ser Thr Thr Pro
    210                 215                 220

Asn Ile Leu Asp Pro Glu Thr Val Gln Arg Val Asp Ser Tyr Thr Gly
225                 230                 235                 240

Tyr Ile Ala Pro Tyr Thr Ser Arg Asn Asn Leu Asn Val Leu Ala Asn
                245                 250                 255

His Thr Val Ser Arg Ile Gln Phe Ala Pro Lys Asn Gly Ser Glu Pro
            260                 265                 270

Leu Lys Ala Thr Gly Val Glu Trp Tyr Pro Thr Gly Asn Lys Asn Gln
        275                 280                 285

Lys Gln Ile Ile Lys Ala Arg Tyr Glu Val Ile Ile Ser Ser Gly Ala
    290                 295                 300

Ile Gly Ser Pro Lys Leu Leu Glu Ile Ser Gly Ile Gly Asn Lys Asp
305                 310                 315                 320

Ile Val Ser Ala Ala Gly Val Glu Ser Leu Ile Asp Leu Pro Gly Val
                325                 330                 335

Gly Ser Asn Met Gln Asp His Val His Ala Ile Thr Val Ser Thr Thr
            340                 345                 350

Asn Ile Thr Gly Tyr Thr Thr Asn Ser Val Phe Val Asn Glu Thr Leu
        355                 360                 365

Ala Gln Glu Gln Arg Glu Glu Tyr Glu Ala Asn Lys Thr Gly Ile Trp
    370                 375                 380

Ala Thr Thr Pro Asn Asn Leu Gly Tyr Pro Thr Pro Glu Gln Leu Phe
385                 390                 395                 400

Asn Gly Thr Glu Phe Val Ser Gly Lys Glu Phe Ala Asp Lys Ile Arg
                405                 410                 415

Asn Ser Thr Asp Glu Trp Ala Asn Tyr Ala Ser Thr Asn Ala Ser
            420                 425                 430

Asn Val Glu Leu Leu Lys Lys Gln Tyr Ala Ile Val Ala Ser Arg Tyr
        435                 440                 445
```

```
Glu Glu Asn Tyr Leu Ser Pro Ile Glu Ile Asn Phe Thr Pro Gly Tyr
    450                 455                 460
Glu Gly Ser Gly Asn Val Asp Leu Gln Asn Asn Lys Tyr Gln Thr Val
465                 470                 475                 480
Asn His Val Leu Ile Ala Pro Leu Ser Arg Gly Tyr Thr His Ile Asn
                485                 490                 495
Ser Ser Asp Val Glu Asp His Ser Val Ile Asn Pro Gln Tyr Tyr Ser
            500                 505                 510
His Pro Met Asp Ile Asp Val His Ile Ala Ser Thr Lys Leu Ala Arg
        515                 520                 525
Glu Ile Ile Thr Ala Ser Pro Gly Leu Gly Asp Ile Asn Ser Gly Glu
    530                 535                 540
Ile Glu Pro Gly Met Asn Ile Thr Ser Glu Asp Asp Leu Arg Ser Trp
545                 550                 555                 560
Leu Ser Asn Asn Val Arg Ser Asp Trp His Pro Val Gly Thr Cys Ala
                565                 570                 575
Met Leu Pro Lys Glu Leu Gly Gly Val Val Ser Pro Ala Leu Met Val
            580                 585                 590
Tyr Gly Thr Ser Asn Leu Arg Val Val Asp Ala Ser Ile Met Pro Leu
        595                 600                 605
Glu Val Ser Ser His Leu Met Gln Pro Thr Tyr Gly Ile Ala Glu Lys
    610                 615                 620
Ala Ala Asp Ile Ile Lys Asn Phe Tyr Lys Thr Gln His Lys Asn Gln
625                 630                 635                 640
Asn

<210> SEQ ID NO 4
<211> LENGTH: 1926
<212> TYPE: DNA
<213> ORGANISM: Mucor prainii

<400> SEQUENCE: 4
atgaagatca cagctgccat tatcactgtt gccacagcat ttgcttcttt tgcttctgct      60
caacaagaca caaattcttc ctcaactgat acttatgatt atgttatcgt tggcggcggt     120
gtagctggtt tggctttggc tagtcgtatc tctgaaaaca aggatgtcac tgttgctgtt     180
ctcgagtccg gtcctaatgc aatgatcaga tttgttgttt atgctcctgg catgtatggc     240
caagctgttg gcactgatct ctgtcctctc attcctacta ctcctcaaga aaatatgggc     300
aacagaagtc tcacaatcgc tactggtaga ttgctcggtg gtggcagtgc tattaatggt     360
ctcgtttgga cccgtggtgg cttgaaggat tacgatgctt gggaggagct cggtaaccct     420
ggatggaacg tgccaacttt gttcaagtac tttaagaagg tcgaaaactt cactcctcct     480
actcctgccc aaattgaata cggcgctact tatcagaaaa gtgctcatgg caagaaggga     540
cctattgatg tctctttcac gaactacgag ttctctcaat tgctagctg aacgcctca     600 ctcgaaaccc ttgatttcac tgcacttcct gatatcttga acggtacttt ggccggttac     660
tctaccactc ccaacatttt ggaccctgag actgttcaac gtgttgattc ctatactggt     720
tacattgctc cttacactag ccgtaacaac ctcaatgttt tggccaacca taccgtctcc     780
cgcattcaat ttgctcccaa gaatggtagc gaacctctca aggctaccgg tgttgaatgg     840
tatcccactg caacaagaa tcaaaagcaa attatcaagg cccgttatga agttatcatc     900
tcatctggtg ccattggtag tcctaagctt ttggaaatct ctggtatcgg taataaggat     960
```

```
atcgtctctg ctgctggtgt cgagtccttg attgacttgc ctggcgttgg ttccaacatg    1020
caagatcacg ttcatgctat cactgtctct actaccaata ttactggcta tactaccaac    1080
agcgtctttg tcaatgaaac ccttgcccaa gaacaaagag aagaatatga agccaacaag    1140
actggtatct gggctactac tcccaacaac ctcggttatc ctacgcccga caactcttc     1200 aatggcaccg aattcgtttc tggaaaggag tttgctgaca agattcgtaa ctctactgat    1260
gaatgggcca actattatgc ttccaccaac gcctccaatg tcgagttatt aaagaagcaa    1320
tatgctattg tcgcctctcg ttacgaagag aactacttgt ctcctattga aatcaacttc    1380
actcctggtt atgagggtag cggtaatgtc gatttgcaaa acaacaagta ccaaactgtc    1440
aaccatgtct tgattgctcc tttaagtcgt ggttatactc acattaactc ttctgatgtg    1500
gaggatcatt ctgtcattaa tccccaatac tactctcatc ctatggatat tgatgtccat    1560
atcgcttcca ctaaacttgc tcgcgaaatc atcactgcct ctcccggtct tggtgacatt    1620
aacagtggcg aaatcgaacc cggtatgaat attacttctg aagacgacct tagatcttgg    1680
ttgagtaata atgtccgttc tgactggcat cctgttggta cttgtgctat gcttcccaag    1740
gaattaggtg gtgttgtcag ccccgctctc atggtttacg gcacttccaa cttgcgtgtt    1800
gttgatgctt cgattatgcc cctcgaagtc tcttctcatt tgatgcaacc cacctacggt    1860
attgctgaga aggctgctga cattattaag aatttctaca agactcaaca caagaaccaa    1920
aattag                                                                1926
```

<210> SEQ ID NO 5
<211> LENGTH: 14
<212> TYPE: PRT
<213> ORGANISM: Mucor prainii

<400> SEQUENCE: 5

Leu Val Glu Asn Phe Thr Pro Pro Thr Pro Ala Gln Ile Glu
1               5                   10

<210> SEQ ID NO 6
<211> LENGTH: 12
<212> TYPE: PRT
<213> ORGANISM: Mucor prainii

<400> SEQUENCE: 6

Ile Arg Asn Ser Thr Asp Glu Trp Ala Asn Tyr Tyr
1               5                   10

<210> SEQ ID NO 7
<211> LENGTH: 21
<212> TYPE: DNA
<213> ORGANISM: Artificial
<220> FEATURE:
<223> OTHER INFORMATION: primer 1 (forward)

<400> SEQUENCE: 7
cchachcchg chcaratyga r                                                21

<210> SEQ ID NO 8
<211> LENGTH: 24
<212> TYPE: DNA
<213> ORGANISM: Artificial
<220> FEATURE:
<223> OTHER INFORMATION: primer 2 (reverse)

<400> SEQUENCE: 8
rtartarttd gcccaytcrt cdgt                                             24

<210> SEQ ID NO 9
<211> LENGTH: 24
<212> TYPE: DNA
<213> ORGANISM: Artificial
<220> FEATURE:
<223> OTHER INFORMATION: primer 3 for 3'-RACE

<400> SEQUENCE: 9
cctacacctg cacaaattga atac                                          24

<210> SEQ ID NO 10
<211> LENGTH: 14
<212> TYPE: DNA
<213> ORGANISM: Artificial
<220> FEATURE:
<223> OTHER INFORMATION: primer 4 for 5'-RACE

<400> SEQUENCE: 10
ggcgttccag ctag                                                     14

<210> SEQ ID NO 11
<211> LENGTH: 20
<212> TYPE: DNA
<213> ORGANISM: Artificial
<220> FEATURE:
<223> OTHER INFORMATION: primer 5 for 5'-RACE

<400> SEQUENCE: 11
caagaaggga cctattgatg                                               20

<210> SEQ ID NO 12
<211> LENGTH: 22
<212> TYPE: DNA
<213> ORGANISM: Artificial
<220> FEATURE:
<223> OTHER INFORMATION: primer 6 for 5'-RACE

<400> SEQUENCE: 12
gagcactttt ctgataagta gc                                            22

<210> SEQ ID NO 13
<211> LENGTH: 22
<212> TYPE: DNA
<213> ORGANISM: Artificial
<220> FEATURE:
<223> OTHER INFORMATION: primer 7 for 5'-RACE

<400> SEQUENCE: 13
cgaactacga gttctctcaa tc                                            22

<210> SEQ ID NO 14
<211> LENGTH: 21
<212> TYPE: DNA
<213> ORGANISM: Artificial
<220> FEATURE:
<223> OTHER INFORMATION: primer 8 for 5'-RACE

<400> SEQUENCE: 14
cgtattcaat ttgtgcaggt g                                             21

<210> SEQ ID NO 15
<211> LENGTH: 18
<212> TYPE: DNA
<213> ORGANISM: Artificial
<220> FEATURE:

<223> OTHER INFORMATION: primer 9 (forward)

<400> SEQUENCE: 15
atgaagatca cagctgcc                                                18

<210> SEQ ID NO 16
<211> LENGTH: 18
<212> TYPE: DNA
<213> ORGANISM: Artificial
<220> FEATURE:
<223> OTHER INFORMATION: primer 10 (reverse)

<400> SEQUENCE: 16
ctaattttgg ttcttgtg                                                18

<210> SEQ ID NO 17
<211> LENGTH: 1926
<212> TYPE: DNA
<213> ORGANISM: Artificial
<220> FEATURE:
<223> OTHER INFORMATION: GDH gene synthesized by using E.coli codon
      usage

<400> SEQUENCE: 17

| | | |
|---|---|---|
| atgaaaatta ccgcggccat tatcaccgtt gcgacggcct ttgcgagctt tgcgtctgcc | 60 |
| cagcaggata ccaacagctc tagtaccgat acgtatgatt acgtgattgt tggcggtggc | 120 |
| gtggcaggtc tggcactggc aagtcgtatt agcgaaaata agatgtgtac cgttgcagtg | 180 |
| ctggaaagcg gtccgaacgc gaatgatcgc tttgtggttt atgccccggg catgtacggt | 240 |
| caggcagttg gcaccgatct gtgcccgctg atcccgacca cgccgcagga aaacatgggt | 300 |
| aatcgtagcc tgaccattgc aacgggtcgt ctgctgggtg gcggttctgc aatcaacggt | 360 |
| ctggtgtgga cccgtggcgg tctgaaagat tatgatgcct gggaagaact gggcaacccg | 420 |
| ggttggaacg cgcaaatct gttcaaatac ttcaaaaaag ttgaaaactt caccccgccg | 480 |
| acgccggccc agattgaata tggcgcaacc taccagaaaa gcgcgcatgg taaaaaaggc | 540 |
| ccgatcgatg tgtcttttac gaactatgaa tttagccagt ctgcgagttg aatgcctct | 600 |
| ctggaaaccc tggatttcac ggcgctgccg gatattctga cggtaccct ggccggctat | 660 |
| agcaccacgc cgaatatcct ggatccggaa acggttcagc gtgtggatag ttataccggt | 720 |
| tacattgcgc cgtacacgag ccgtaacaat ctgaacgttc tggcaaatca caccgtgtct | 780 |
| cgcatccagt ttgcgccgaa aaacggcagt gaaccgctga agccaccgg tgttgaatgg | 840 |
| tatccgacgg gcaacaaaaa ccagaaacag atcatcaaag cacgctacga agtgattatc | 900 |
| agctctggtg cgattggctc tccgaaactg ctggaaatta gtggcatcgg taataaagat | 960 |
| attgttagtg cagcgggtgt ggaaagcctg atcgatctgc cggcgtggg tagcaacatg | 1020 |
| caggatcatg ttcacgcgat accgtgagt accacgaata tcacgggcta taccacgaac | 1080 |
| agcgttttg tgaatgaaac cctggcccag aacagcgtg aagaatatga agcgaacaaa | 1140 |
| acgggtattt gggccaccac gccgaacaat ctgggctacc cgaccccgga acagctgttt | 1200 |
| aatggtacgg aatttgtgtc tggcaaagaa tttgcggata aaattcgtaa cagtaccgat | 1260 |
| gaatgggcaa attattacgc gagcacgaac gcctctaatg ttgaactgct gaaaaaacag | 1320 |
| tatgccatcg tggcaagccg ctatgaagaa aactacctgt ctccgattga aatcaatttt | 1380 |
| accccgggtt atgaaggcag cggtaacgtt gatctgcaga acaataaata ccagaccgtt | 1440 |
| aatcatgtgc tgattgcgcc gctgagccgt ggctatacgc atatcaacag tagcgatgtt | 1500 |

```
gaagatcaca gtgtgattaa tccgcagtat tacagccatc cgatggatat tgatgtgcac   1560
atcgcaagca ccaaactggc gcgcgaaatt atcacggcgt ctccgggcct gggtgatatt   1620
aacagtggtg aaatcgaacc gggcatgaat atcaccagtg aagatgatct gcgttcttgg   1680
ctgagtaaca atgttcgcag cgattggcac ccggtgggta cctgtgcgat gctgccgaaa   1740
gaactgggcg gtgtggttag cccggccctg atggtttatg caccagcaa cctgcgcgtg   1800 gttgatgcat ctattatgcc gctggaagtg tctagtcatc tgatgcagcc gacctatggc   1860
atcgccgaaa aagccgcaga tatcatcaaa aacttctaca aacccagca caaaaaccag   1920 aattaa                                                              1926

<210> SEQ ID NO 18
<211> LENGTH: 36
<212> TYPE: DNA
<213> ORGANISM: Artificial
<220> FEATURE:
<223> OTHER INFORMATION: primer Mp wild (forward)

<400> SEQUENCE: 18
aaggagatat acatatgaaa attaccgcgg ccatta                              36

<210> SEQ ID NO 19
<211> LENGTH: 34
<212> TYPE: DNA
<213> ORGANISM: Artificial
<220> FEATURE:
<223> OTHER INFORMATION: primer Mp NS1 (forward)

<400> SEQUENCE: 19
aaggagatat acatatgcag caggatacca acag                                34

<210> SEQ ID NO 20
<211> LENGTH: 36
<212> TYPE: DNA
<213> ORGANISM: Artificial
<220> FEATURE:
<223> OTHER INFORMATION: primer Mp NS2 (forward)

<400> SEQUENCE: 20
aaggagatat acatatgcag gataccaaca gctcta                              36

<210> SEQ ID NO 21
<211> LENGTH: 37
<212> TYPE: DNA
<213> ORGANISM: Artificial
<220> FEATURE:
<223> OTHER INFORMATION: primer Mp (reverse)

<400> SEQUENCE: 21
gctcgaattc ggatccttaa ttctggtttt tgtgctg                             37

<210> SEQ ID NO 22
<211> LENGTH: 1869
<212> TYPE: DNA
<213> ORGANISM: Artificial
<220> FEATURE:
<223> OTHER INFORMATION: NS1

<400> SEQUENCE: 22
atgcagcagg ataccaacag ctctagtacc gatacgtatg attacgtgat tgttggcggt    60
ggcgtggcag gtctggcact ggcaagtcgt attagcgaaa ataaagatgt gaccgttgca   120
gtgctggaaa gcggtccgaa cgcgaatgat cgctttgtgg tttatgcccc gggcatgtac   180
```

```
ggtcaggcag ttggcaccga tctgtgcccg ctgatcccga ccacgccgca ggaaaacatg    240
ggtaatcgta gcctgaccat tgcaacgggt cgtctgctgg gtggcggttc tgcaatcaac    300
ggtctggtgt ggacccgtgg cggtctgaaa gattatgatg cctgggaaga actgggcaac    360
ccgggttgga acggcgcaaa tctgttcaaa tacttcaaaa aagttgaaaa cttcaccccg    420
ccgacgccgg cccagattga atatggcgca acctaccaga aaagcgcgca tggtaaaaaa    480
ggcccgatcg atgtgtcttt tacgaactat gaatttagcc agtctgcgag ttggaatgcc    540
tctctggaaa ccctggattt cacggcgctg ccggatattc tgaacggtac cctggccggc    600
tatagcacca cgccgaatat cctggatccg gaaacggttc agcgtgtgga tagttatacc    660
ggttacattg cgccgtacac gagccgtaac aatctgaacg ttctggcaaa tcacaccgtg    720
tctcgcatcc agtttgcgcc gaaaaacggc agtgaaccgc tgaaagccac cggtgttgaa    780
tggtatccga cgggcaacaa aaaccagaaa cagatcatca agcacgcta cgaagtgatt    840 atcagctctg gtgcgattgg ctctccgaaa ctgctggaaa ttagtggcat cggtaataaa    900
gatattgtta gtgcagcggg tgtggaaagc ctgatcgatc tgccgggcgt gggtagcaac    960
atgcaggatc atgttcacgc gattaccgtg agtaccacga atatcacggg ctataccacg   1020
aacagcgttt ttgtgaatga aaccctggcc caggaacagc gtgaagaata tgaagcgaac   1080
aaaacgggta tttgggccac cacgccgaac aatctgggct acccgacccc ggaacagctg   1140
tttaatggta cggaatttgt gtctggcaaa gaatttgcgg ataaaattcg taacagtacc   1200
gatgaatggg caattatta cgcgagcacg aacgcctcta atgttgaact gctgaaaaaa   1260
cagtatgcca tcgtggcaag ccgctatgaa gaaaactacc tgtctccgat tgaaatcaat   1320 tttacccccgg ttatgaagg cagcggtaac gttgatctgc agaacaataa ataccagacc   1380
gttaatcatg tgctgattgc gccgctgagc cgtggctata cgcatatcaa cagtagcgat   1440
gttgaagatc acagtgtgat taatccgcag tattacagcc atccgatgga tattgatgtg   1500
cacatcgcaa gcaccaaact ggcgcgcgaa attatcacgg cgtctccggg cctgggtgat   1560
attaacagtg gtgaaatcga accgggcatg aatatcacca gtgaagatga tctgcgttct   1620
tggctgagta acaatgttcg cagcgattgg cacccggtgg gtacctgtgc gatgctgccg   1680
aaagaactgg gcggtgtggt tagcccggcc ctgatggttt atggcaccag caacctgcgc   1740
gtggttgatg catctattat gccgctggaa gtgtctagtc atctgatgca gccgacctat   1800
ggcatcgccg aaaagccgc agatatcatc aaaaacttct acaaacccca gcacaaaaac   1860
cagaattaa                                                            1869
```

<210> SEQ ID NO 23
<211> LENGTH: 622
<212> TYPE: PRT
<213> ORGANISM: Artificial
<220> FEATURE:
<223> OTHER INFORMATION: NS1

<400> SEQUENCE: 23

Met Gln Gln Asp Thr Asn Ser Ser Thr Asp Thr Tyr Asp Tyr Val
1               5                   10                  15

Ile Val Gly Gly Gly Val Ala Gly Leu Ala Leu Ala Ser Arg Ile Ser
                20                  25                  30

Glu Asn Lys Asp Val Thr Val Ala Val Leu Glu Ser Gly Pro Asn Ala
            35                  40                  45

Asn Asp Arg Phe Val Val Tyr Ala Pro Gly Met Tyr Gly Gln Ala Val

-continued

```
                50                  55                  60
Gly Thr Asp Leu Cys Pro Leu Ile Pro Thr Thr Pro Gln Glu Asn Met
 65                  70                  75                  80

Gly Asn Arg Ser Leu Thr Ile Ala Thr Gly Arg Leu Leu Gly Gly Gly
                 85                  90                  95

Ser Ala Ile Asn Gly Leu Val Trp Thr Arg Gly Leu Lys Asp Tyr
                100                 105                 110

Asp Ala Trp Glu Glu Leu Gly Asn Pro Gly Trp Asn Gly Ala Asn Leu
                115                 120                 125

Phe Lys Tyr Phe Lys Lys Val Glu Asn Phe Thr Pro Pro Thr Pro Ala
130                 135                 140

Gln Ile Glu Tyr Gly Ala Thr Tyr Gln Lys Ser Ala His Gly Lys Lys
145                 150                 155                 160

Gly Pro Ile Asp Val Ser Phe Thr Asn Tyr Glu Phe Ser Gln Ser Ala
                165                 170                 175

Ser Trp Asn Ala Ser Leu Glu Thr Leu Asp Phe Thr Ala Leu Pro Asp
                180                 185                 190

Ile Leu Asn Gly Thr Leu Ala Gly Tyr Ser Thr Thr Pro Asn Ile Leu
                195                 200                 205

Asp Pro Glu Thr Val Gln Arg Val Asp Ser Tyr Thr Gly Tyr Ile Ala
210                 215                 220

Pro Tyr Thr Ser Arg Asn Asn Leu Asn Val Leu Ala Asn His Thr Val
225                 230                 235                 240

Ser Arg Ile Gln Phe Ala Pro Lys Asn Gly Ser Glu Pro Leu Lys Ala
                245                 250                 255

Thr Gly Val Glu Trp Tyr Pro Thr Gly Asn Lys Asn Gln Lys Gln Ile
                260                 265                 270

Ile Lys Ala Arg Tyr Glu Val Ile Ile Ser Ser Gly Ala Ile Gly Ser
                275                 280                 285

Pro Lys Leu Leu Glu Ile Ser Gly Ile Gly Asn Lys Asp Ile Val Ser
                290                 295                 300

Ala Ala Gly Val Glu Ser Leu Ile Asp Leu Pro Gly Val Gly Ser Asn
305                 310                 315                 320

Met Gln Asp His Val His Ala Ile Thr Val Ser Thr Thr Asn Ile Thr
                325                 330                 335

Gly Tyr Thr Thr Asn Ser Val Phe Val Asn Glu Thr Leu Ala Gln Glu
                340                 345                 350

Gln Arg Glu Glu Tyr Glu Ala Asn Lys Thr Gly Ile Trp Ala Thr Thr
                355                 360                 365

Pro Asn Asn Leu Gly Tyr Pro Thr Pro Glu Gln Leu Phe Asn Gly Thr
370                 375                 380

Glu Phe Val Ser Gly Lys Glu Phe Ala Asp Lys Ile Arg Asn Ser Thr
385                 390                 395                 400

Asp Glu Trp Ala Asn Tyr Tyr Ala Ser Thr Asn Ala Ser Asn Val Glu
                405                 410                 415

Leu Leu Lys Lys Gln Tyr Ala Ile Val Ala Ser Arg Tyr Glu Glu Asn
                420                 425                 430

Tyr Leu Ser Pro Ile Glu Ile Asn Phe Thr Pro Gly Tyr Glu Gly Ser
                435                 440                 445

Gly Asn Val Asp Leu Gln Asn Asn Lys Tyr Gln Thr Val Asn His Val
                450                 455                 460

Leu Ile Ala Pro Leu Ser Arg Gly Tyr Thr His Ile Asn Ser Ser Asp
465                 470                 475                 480
```

Val Glu Asp His Ser Val Ile Asn Pro Gln Tyr Tyr Ser His Pro Met
                485                 490                 495

Asp Ile Asp Val His Ile Ala Ser Thr Lys Leu Ala Arg Glu Ile Ile
            500                 505                 510

Thr Ala Ser Pro Gly Leu Gly Asp Ile Asn Ser Gly Glu Ile Glu Pro
            515                 520                 525

Gly Met Asn Ile Thr Ser Glu Asp Asp Leu Arg Ser Trp Leu Ser Asn
            530                 535                 540

Asn Val Arg Ser Asp Trp His Pro Val Gly Thr Cys Ala Met Leu Pro
545                 550                 555                 560

Lys Glu Leu Gly Gly Val Val Ser Pro Ala Leu Met Val Tyr Gly Thr
                565                 570                 575

Ser Asn Leu Arg Val Val Asp Ala Ser Ile Met Pro Leu Glu Val Ser
            580                 585                 590

Ser His Leu Met Gln Pro Thr Tyr Gly Ile Ala Glu Lys Ala Ala Asp
            595                 600                 605

Ile Ile Lys Asn Phe Tyr Lys Thr Gln His Lys Asn Gln Asn
    610                 615                 620

<210> SEQ ID NO 24
<211> LENGTH: 1866
<212> TYPE: DNA
<213> ORGANISM: Artificial
<220> FEATURE:
<223> OTHER INFORMATION: NS2

<400> SEQUENCE: 24
atgcaggata ccaacagctc tagtaccgat acgtatgatt acgtgattgt tggcggtggc      60
gtggcaggtc tggcactggc aagtcgtatt agcgaaaata agatgtgac cgttgcagtg     120 ctggaaagcg gtccgaacgc gaatgatcgc tttgtggttt atgccccggg catgtacggt     180
caggcagttg gcaccgatct gtgcccgctg atccccgacca cgccgcagga aaacatgggt     240
aatcgtagcc tgaccattgc aacgggtcgt ctgctgggtg gcggttctgc aatcaacggt     300
ctggtgtgga cccgtggcgg tctgaaagat tatgatgcct gggaagaact gggcaacccg     360
ggttggaacg gcgcaaatct gttcaaatac ttcaaaaaag ttgaaaactt caccccgccg     420
acgccggccc agattgaata tggcgcaacc taccagaaaa gcgcgcatgg taaaaaggc     480 ccgatcgatg tgtcttttac gaactatgaa tttagccagt ctgcgagttg aatgcctct     540 ctggaaaccc tggatttcac ggcgctgccg gatattctga acggtaccct ggccggctat     600
agcaccacgc cgaatatcct ggatccggaa acggttcagc gtgtggatag ttataccggt     660
tacattgcgc cgtacacgag ccgtaacaat ctgaacgttc tggcaaatca caccgtgtct     720
cgcatccagt ttgcgccgaa aaacggcagt gaaccgctga agccaccgg tgttgaatgg     780 tatccgacgg caacaaaaa ccagaaacag atcatcaaag cacgctacga agtgattatc     840
agctctggtg cgattggctc tccgaaactg ctggaaatta gtggcatcgg taataaagat     900
attgttagtg cagcgggtgt ggaaagcctg atcgatctgc cgggcgtggg tagcaacatg     960
caggatcatg ttcacgcgat accgtgagt accacgaata tcacgggcta taccacgaac    1020
agcgtttttg tgaatgaaac cctggcccag gaacagcgtg aagaatatga agcgaacaaa    1080
acgggtattt ggccaccac gccgaacaat ctgggctacc cgaccccgga acagctgttt    1140
aatggtacgg aatttgtgtc tggcaaagaa tttgcggata aaattcgtaa cagtaccgat    1200
gaatgggcaa attattacgc gagcacgaac gcctctaatg ttgaactgct gaaaaaacag    1260

```
tatgccatcg tggcaagccg ctatgaagaa aactacctgt ctccgattga aatcaatttt    1320
accccgggtt atgaaggcag cggtaacgtt gatctgcaga acaataaata ccagaccgtt    1380
aatcatgtgc tgattgcgcc gctgagccgt ggctatacgc atatcaacag tagcgatgtt    1440
gaagatcaca gtgtgattaa tccgcagtat tacagccatc cgatggatat tgatgtgcac    1500
atcgcaagca ccaaactggc gcgcgaaatt atcacggcgt ctccgggcct gggtgatatt    1560
aacagtggtg aaatcgaacc gggcatgaat atcaccagtg aagatgatct gcgttcttgg    1620
ctgagtaaca atgttcgcag cgattggcac ccggtgggta cctgtgcgat gctgccgaaa    1680
gaactgggcg gtgtggttag cccggccctg atggtttatg caccagcaa cctgcgcgtg    1740 gttgatgcat ctattatgcc gctggaagtg tctagtcatc tgatgcagcc gacctatggc    1800
atcgccgaaa aagccgcaga tatcatcaaa aacttctaca aacccagca caaaaaccag    1860 aattaa                                                                1866
```

<210> SEQ ID NO 25
<211> LENGTH: 621
<212> TYPE: PRT
<213> ORGANISM: Artificial
<220> FEATURE:
<223> OTHER INFORMATION: NS2

<400> SEQUENCE: 25

```
Met Gln Asp Thr Asn Ser Ser Thr Asp Thr Tyr Asp Tyr Val Ile
1               5                   10                  15

Val Gly Gly Gly Val Ala Gly Leu Ala Leu Ala Ser Arg Ile Ser Glu
            20                  25                  30

Asn Lys Asp Val Thr Val Ala Val Leu Glu Ser Gly Pro Asn Ala Asn
        35                  40                  45

Asp Arg Phe Val Val Tyr Ala Pro Gly Met Tyr Gly Gln Ala Val Gly
    50                  55                  60

Thr Asp Leu Cys Pro Leu Ile Pro Thr Pro Gln Glu Asn Met Gly
65                  70                  75                  80

Asn Arg Ser Leu Thr Ile Ala Thr Gly Arg Leu Leu Gly Gly Ser
                85                  90                  95

Ala Ile Asn Gly Leu Val Trp Thr Arg Gly Gly Leu Lys Asp Tyr Asp
            100                 105                 110

Ala Trp Glu Glu Leu Gly Asn Pro Gly Trp Asn Gly Ala Asn Leu Phe
        115                 120                 125

Lys Tyr Phe Lys Lys Val Glu Asn Phe Thr Pro Pro Thr Pro Ala Gln
    130                 135                 140

Ile Glu Tyr Gly Ala Thr Tyr Gln Lys Ser Ala His Gly Lys Lys Gly
145                 150                 155                 160

Pro Ile Asp Val Ser Phe Thr Asn Tyr Glu Phe Ser Gln Ser Ala Ser
                165                 170                 175

Trp Asn Ala Ser Leu Glu Thr Leu Asp Phe Thr Ala Leu Pro Asp Ile
            180                 185                 190

Leu Asn Gly Thr Leu Ala Gly Tyr Ser Thr Thr Pro Asn Ile Leu Asp
        195                 200                 205

Pro Glu Thr Val Gln Arg Val Asp Ser Tyr Thr Gly Tyr Ile Ala Pro
    210                 215                 220

Tyr Thr Ser Arg Asn Asn Leu Asn Val Leu Ala Asn His Thr Val Ser
225                 230                 235                 240

Arg Ile Gln Phe Ala Pro Lys Asn Gly Ser Glu Pro Leu Lys Ala Thr
```

245                 250                 255
Gly Val Glu Trp Tyr Pro Thr Gly Asn Lys Asn Gln Lys Gln Ile Ile
            260                 265                 270

Lys Ala Arg Tyr Glu Val Ile Ile Ser Ser Gly Ala Ile Gly Ser Pro
        275                 280                 285

Lys Leu Leu Glu Ile Ser Gly Ile Gly Asn Lys Asp Ile Val Ser Ala
        290                 295                 300

Ala Gly Val Glu Ser Leu Ile Asp Leu Pro Gly Val Gly Ser Asn Met
305                 310                 315                 320

Gln Asp His Val His Ala Ile Thr Val Ser Thr Thr Asn Ile Thr Gly
                325                 330                 335

Tyr Thr Thr Asn Ser Val Phe Val Asn Glu Thr Leu Ala Gln Glu Gln
                340                 345                 350

Arg Glu Glu Tyr Glu Ala Asn Lys Thr Gly Ile Trp Ala Thr Thr Pro
            355                 360                 365

Asn Asn Leu Gly Tyr Pro Thr Pro Glu Gln Leu Phe Asn Gly Thr Glu
        370                 375                 380

Phe Val Ser Gly Lys Glu Phe Ala Asp Lys Ile Arg Asn Ser Thr Asp
385                 390                 395                 400

Glu Trp Ala Asn Tyr Tyr Ala Ser Thr Asn Ala Ser Asn Val Glu Leu
                405                 410                 415

Leu Lys Lys Gln Tyr Ala Ile Val Ala Ser Arg Tyr Glu Glu Asn Tyr
            420                 425                 430

Leu Ser Pro Ile Glu Ile Asn Phe Thr Pro Gly Tyr Glu Gly Ser Gly
        435                 440                 445

Asn Val Asp Leu Gln Asn Asn Lys Tyr Gln Thr Val Asn His Val Leu
    450                 455                 460

Ile Ala Pro Leu Ser Arg Gly Tyr Thr His Ile Asn Ser Ser Asp Val
465                 470                 475                 480

Glu Asp His Ser Val Ile Asn Pro Gln Tyr Tyr Ser His Pro Met Asp
                485                 490                 495

Ile Asp Val His Ile Ala Ser Thr Lys Leu Ala Arg Glu Ile Ile Thr
            500                 505                 510

Ala Ser Pro Gly Leu Gly Asp Ile Asn Ser Gly Glu Ile Glu Pro Gly
        515                 520                 525

Met Asn Ile Thr Ser Glu Asp Leu Arg Ser Trp Leu Ser Asn Asn
    530                 535                 540

Val Arg Ser Asp Trp His Pro Val Gly Thr Cys Ala Met Leu Pro Lys
545                 550                 555                 560

Glu Leu Gly Gly Val Val Ser Pro Ala Leu Met Val Tyr Gly Thr Ser
                565                 570                 575

Asn Leu Arg Val Val Asp Ala Ser Ile Met Pro Leu Glu Val Ser Ser
            580                 585                 590

His Leu Met Gln Pro Thr Tyr Gly Ile Ala Glu Lys Ala Ala Asp Ile
        595                 600                 605

Ile Lys Asn Phe Tyr Lys Thr Gln His Lys Asn Gln Asn
610                 615                 620

<210> SEQ ID NO 26
<211> LENGTH: 30
<212> TYPE: DNA
<213> ORGANISM: Artificial
<220> FEATURE:
<223> OTHER INFORMATION: primer Mp NS3 (forward)

<400> SEQUENCE: 26
ggataccaac catatgagta ccgatacgta                                    30

<210> SEQ ID NO 27
<211> LENGTH: 26
<212> TYPE: DNA
<213> ORGANISM: Artificial
<220> FEATURE:
<223> OTHER INFORMATION: primer Mp NS3 (reverse)

<400> SEQUENCE: 27
gcggtaattt tcatatgtat atctcc                                        26

<210> SEQ ID NO 28
<211> LENGTH: 30
<212> TYPE: DNA
<213> ORGANISM: Artificial
<220> FEATURE:
<223> OTHER INFORMATION: primer Mp NS4 (forward)

<400> SEQUENCE: 28
ggataccaac agccatatga ccgatacgta                                    30

<210> SEQ ID NO 29
<211> LENGTH: 1848
<212> TYPE: DNA
<213> ORGANISM: Artificial
<220> FEATURE:
<223> OTHER INFORMATION: NS3

<400> SEQUENCE: 29
atgagtaccg atacgtatga ttacgtgacg gttggcggtg gcgtggcagg tctggcactg      60
gcaagtcgta ttagcgaaaa taaagatgtg accgttgcag tgctggaaag cggtccgaac     120
gcgaatgatc gctttgtggt ttatgccccg ggcatgtacg gtcaggcagt tggcaccgat     180
ctgtgcccgc tgatcccgac cacgccgcag gaaaacatgg gtaatcgtag cctgaccatt     240
gcaacgggtc gtctgctggg tgcggttct gcaatcaacg gtctggtgtg gacccgtggc     300
ggtctgaaag attatgatgc ctgggaagaa ctgggcaacc cgggttggaa cggcgcaaat     360
ctgttcaaat acttcaaaaa agttgaaaac ttcaccccgc cgacgccggc ccagattgaa     420
tatggcgcaa cctaccagaa aagcgcgcat ggtaaaaaag cccgatcga tgtgtctttt     480 acgaactatg aatttagcca gtctgcgagt tggaatgcct ctctggaaac cctggatttc     540
acggcgctgc cggatattct gaacggtacc ctggccggct atagcaccac gccgaatatc     600
ctggatccgg aaacggttca gcgtgtggat agttataccg gttacattgc gccgtacacg     660
agccgtaaca atctgaacgt tctggcaaat cacaccgtgt ctcgcatcca gtttgcgccg     720
aaaaacggca gtgaaccgct gaaagccacc ggtgttgaat ggtatccgac gggcaacaaa     780
aaccagaaac agatcatcaa agcacgctac gaagtgatta tcagctctgg tgcgattggc     840
tctccgaaac tgctggaaat tagtggcatc ggtaataaag atattgttag tgcagcgggt     900
gtggaaagcc tgatcgatct gccgggcgtg ggtagcaaca tgcaggatca tgttcacgcg     960
attaccgtga gtaccacgaa tatcacgggc tataccacga cagcgttttt tgtgaatgaa    1020
accctggccc aggaacagcg tgaagaatat gaagcgaaca aaacgggtat ttgggccacc    1080
acgccgaaca atctgggcta cccgaccccg gaacagctgt ttaatggtac ggaatttgtg    1140
tctggcaaag aatttgcgga taaaattcgt aacagtaccg atgaatgggc aaattattac    1200
gcgagcacga acgcctctaa tgttgaactg ctgaaaaaac agtatgccat cgtggcaagc    1260

```
cgctatgaag aaaactacct gtctccgatt gaaatcaatt ttaccccggg ttatgaaggc   1320
agcggtaacg ttgatctgca gaacaataaa taccagaccg ttaatcatgt gctgattgcg   1380
ccgctgagcc gtggctatac gcatatcaac agtagcgatg ttgaagatca cagtgtgatt   1440
aatccgcagt attacagcca tccgatggat attgatgtgc acatcgcaag caccaaactg   1500
gcgcgcgaaa ttatcacggc gtctccgggc ctgggtgata ttaacagtgg tgaaatcgaa   1560
ccgggcatga atatcaccag tgaagatgat ctgcgttctt ggctgagtaa caatgttcgc   1620
agcgattggc acccggtggg tacctgtgcg atgctgccga agaactggg cggtgtggtt   1680 agcccggccc tgatggttta tggcaccagc aacctgcgcg tggttgatgc atctattatg   1740
ccgctggaag tgtctagtca tctgatgcag ccgacctatg gcatcgccga aaaagccgca   1800
gatatcatca aaaacttcta caaaacccag cacaaaaacc agaattaa              1848
```

<210> SEQ ID NO 30
<211> LENGTH: 615
<212> TYPE: PRT
<213> ORGANISM: Artificial
<220> FEATURE:
<223> OTHER INFORMATION: NS3

<400> SEQUENCE: 30

```
Met Ser Thr Asp Thr Tyr Asp Tyr Val Ile Val Gly Gly Val Ala
1               5                   10                  15

Gly Leu Ala Leu Ala Ser Arg Ile Ser Glu Asn Lys Asp Val Thr Val
            20                  25                  30

Ala Val Leu Glu Ser Gly Pro Asn Ala Asn Asp Arg Phe Val Val Tyr
        35                  40                  45

Ala Pro Gly Met Tyr Gly Gln Ala Val Gly Thr Asp Leu Cys Pro Leu
    50                  55                  60

Ile Pro Thr Thr Pro Gln Glu Asn Met Gly Asn Arg Ser Leu Thr Ile
65                  70                  75                  80

Ala Thr Gly Arg Leu Leu Gly Gly Gly Ser Ala Ile Asn Gly Leu Val
                85                  90                  95

Trp Thr Arg Gly Gly Leu Lys Asp Tyr Asp Ala Trp Glu Glu Leu Gly
            100                 105                 110

Asn Pro Gly Trp Asn Gly Ala Asn Leu Phe Lys Tyr Phe Lys Lys Val
        115                 120                 125

Glu Asn Phe Thr Pro Pro Thr Pro Ala Gln Ile Glu Tyr Gly Ala Thr
    130                 135                 140

Tyr Gln Lys Ser Ala His Gly Lys Lys Gly Pro Ile Asp Val Ser Phe
145                 150                 155                 160

Thr Asn Tyr Glu Phe Ser Gln Ser Ala Ser Trp Asn Ala Ser Leu Glu
                165                 170                 175

Thr Leu Asp Phe Thr Ala Leu Pro Asp Ile Leu Asn Gly Thr Leu Ala
            180                 185                 190

Gly Tyr Ser Thr Thr Pro Asn Ile Leu Asp Pro Glu Thr Val Gln Arg
        195                 200                 205

Val Asp Ser Tyr Thr Gly Tyr Ile Ala Pro Tyr Thr Ser Arg Asn Asn
    210                 215                 220

Leu Asn Val Leu Ala Asn His Thr Val Ser Arg Ile Gln Phe Ala Pro
225                 230                 235                 240

Lys Asn Gly Ser Glu Pro Leu Lys Ala Thr Gly Val Glu Trp Tyr Pro
                245                 250                 255
```

Thr Gly Asn Lys Asn Gln Lys Gln Ile Ile Lys Ala Arg Tyr Glu Val
                260                 265                 270

Ile Ile Ser Ser Gly Ala Ile Gly Ser Pro Lys Leu Leu Glu Ile Ser
            275                 280                 285

Gly Ile Gly Asn Lys Asp Ile Val Ser Ala Ala Gly Val Glu Ser Leu
        290                 295                 300

Ile Asp Leu Pro Gly Val Gly Ser Asn Met Gln Asp His Val His Ala
305                 310                 315                 320

Ile Thr Val Ser Thr Thr Asn Ile Thr Gly Tyr Thr Thr Asn Ser Val
                325                 330                 335

Phe Val Asn Glu Thr Leu Ala Gln Glu Gln Arg Glu Glu Tyr Glu Ala
                340                 345                 350

Asn Lys Thr Gly Ile Trp Ala Thr Thr Pro Asn Asn Leu Gly Tyr Pro
            355                 360                 365

Thr Pro Glu Gln Leu Phe Asn Gly Thr Glu Phe Val Ser Gly Lys Glu
        370                 375                 380

Phe Ala Asp Lys Ile Arg Asn Ser Thr Asp Glu Trp Ala Asn Tyr Tyr
385                 390                 395                 400

Ala Ser Thr Asn Ala Ser Asn Val Glu Leu Leu Lys Lys Gln Tyr Ala
                405                 410                 415

Ile Val Ala Ser Arg Tyr Glu Glu Asn Tyr Leu Ser Pro Ile Glu Ile
                420                 425                 430

Asn Phe Thr Pro Gly Tyr Glu Gly Ser Gly Asn Val Asp Leu Gln Asn
            435                 440                 445

Asn Lys Tyr Gln Thr Val Asn His Val Leu Ile Ala Pro Leu Ser Arg
        450                 455                 460

Gly Tyr Thr His Ile Asn Ser Ser Asp Val Glu Asp His Ser Val Ile
465                 470                 475                 480

Asn Pro Gln Tyr Tyr Ser His Pro Met Asp Ile Asp Val His Ile Ala
                485                 490                 495

Ser Thr Lys Leu Ala Arg Glu Ile Ile Thr Ala Ser Pro Gly Leu Gly
                500                 505                 510

Asp Ile Asn Ser Gly Glu Ile Glu Pro Gly Met Asn Ile Thr Ser Glu
            515                 520                 525

Asp Asp Leu Arg Ser Trp Leu Ser Asn Asn Val Arg Ser Asp Trp His
        530                 535                 540

Pro Val Gly Thr Cys Ala Met Leu Pro Lys Glu Leu Gly Gly Val Val
545                 550                 555                 560

Ser Pro Ala Leu Met Val Tyr Gly Thr Ser Asn Leu Arg Val Val Asp
                565                 570                 575

Ala Ser Ile Met Pro Leu Glu Val Ser Ser His Leu Met Gln Pro Thr
                580                 585                 590

Tyr Gly Ile Ala Glu Lys Ala Ala Asp Ile Ile Lys Asn Phe Tyr Lys
            595                 600                 605

Thr Gln His Lys Asn Gln Asn
        610                 615

<210> SEQ ID NO 31
<211> LENGTH: 1845
<212> TYPE: DNA
<213> ORGANISM: Artificial
<220> FEATURE:
<223> OTHER INFORMATION: NS4

<400> SEQUENCE: 31

```
atgaccgata cgtatgatta cgtgacggtt ggcggtggcg tggcaggtct ggcactggca      60
agtcgtatta gcgaaaataa agatgtgacc gttgcagtgc tggaaagcgg tccgaacgcg     120
aatgatcgct ttgtggttta tgccccgggc atgtacggtc aggcagttgg caccgatctg     180
tgcccgctga tcccgaccac gccgcaggaa acatgggta atcgtagcct gaccattgca      240
acgggtcgtc tgctgggtgg cggttctgca atcaacggtc tggtgtggac ccgtggcggt     300
ctgaaagatt atgatgcctg gaagaactg gcaacccgg ttggaacgg cgcaaatctg        360
ttcaaatact tcaaaaaagt tgaaaacttc accccgccga cgccggccca gattgaatat     420
ggcgcaacct accagaaaag cgcgcatggt aaaaaaggcc cgatcgatgt gtcttttacg     480
aactatgaat ttagccagtc tgcgagttgg aatgcctctc tggaaaccct ggatttcacg     540
gcgctgccgg atattctgaa cggtaccctg gccggctata gcaccacgcc gaatatcctg     600
gatccggaaa cggttcagcg tgtggatagt ataccggtt acattgcgcc gtacacgagc      660
cgtaacaatc tgaacgttct ggcaaatcac accgtgtctc gcatccagtt tgcgccgaaa     720
aacggcagtg aaccgctgaa agccaccggt gttgaatggt atccgacggg caacaaaaac    780
cagaaacaga tcatcaaagc acgctacgaa gtgattatca gctctggtgc gattggctct     840
ccgaaactgc tggaaattag tggcatcggt aataaagata ttgttagtgc agcgggtgtg    900
gaaagcctga tcgatctgcc gggcgtgggt agcaacatgc aggatcatgt tcacgcgatt    960
accgtgagta ccacgaatat cacgggctat accacgaaca cgttttttgt gaatgaaacc   1020
ctggcccagg aacagcgtga agaatatgaa gcgaacaaaa cgggtatttg gccaccacg    1080
ccgaacaatc tgggctaccc gaccccggaa cagctgttta tggtacgga atttgtgtct    1140
ggcaaagaat ttgcggataa aattcgtaac agtaccgatg aatgggcaaa ttattacgcg   1200
agcacgaacg cctctaatgt tgaactgctg aaaaaacagt atgccatcgt ggcaagccgc   1260
tatgaagaaa actacctgtc tccgattgaa atcaatttta ccccgggtta tgaaggcagc   1320
ggtaacgttg atctgcagaa caataaatac cagaccgtta tcatgtgct gattgcgccg    1380
ctgagccgtg gctatacgca tatcaacagt agcgatgttg aagatcacag tgtgattaat   1440
ccgcagtatt acagccatcc gatggatatt gatgtgcaca tcgcaagcac caaactggcg   1500
cgcgaaatta tcacggcgtc tccgggcctg ggtgatatta acagtggtga aatcgaaccg   1560
ggcatgaata tcaccagtga agatgatctg cgttcttggc tgagtaacaa tgttcgcagc   1620
gattggcacc cggtgggtac ctgtgcgatg ctgccgaaag aactgggcgg tgtggttagc   1680
ccggccctga tggtttatgg caccagcaac ctgcgcgtgg ttgatgcatc tattatgccg   1740
ctggaagtgt ctagtcatct gatgcagccg acctatggca tcgccgaaaa agccgcagat   1800
atcatcaaaa acttctacaa aacccagcac aaaaaccaga attaa                    1845
```

<210> SEQ ID NO 32
<211> LENGTH: 614
<212> TYPE: PRT
<213> ORGANISM: Artificial
<220> FEATURE:
<223> OTHER INFORMATION: NS4

<400> SEQUENCE: 32

Met Thr Asp Thr Tyr Asp Tyr Val Ile Val Gly Gly Gly Val Ala Gly
1               5                   10                  15

Leu Ala Leu Ala Ser Arg Ile Ser Glu Asn Lys Asp Val Thr Val Ala
            20                  25                  30

Val Leu Glu Ser Gly Pro Asn Ala Asn Asp Arg Phe Val Val Tyr Ala

```
            35                  40                  45
Pro Gly Met Tyr Gly Gln Ala Val Gly Thr Asp Leu Cys Pro Leu Ile
 50                  55                  60
Pro Thr Thr Pro Gln Glu Asn Met Gly Asn Arg Ser Leu Thr Ile Ala
 65                  70                  75                  80
Thr Gly Arg Leu Leu Gly Gly Ser Ala Ile Asn Gly Leu Val Trp
                 85                  90                  95
Thr Arg Gly Gly Leu Lys Asp Tyr Asp Ala Trp Glu Glu Leu Gly Asn
                100                 105                 110
Pro Gly Trp Asn Gly Ala Asn Leu Phe Lys Tyr Phe Lys Lys Val Glu
            115                 120                 125
Asn Phe Thr Pro Pro Thr Pro Ala Gln Ile Glu Tyr Gly Ala Thr Tyr
130                 135                 140
Gln Lys Ser Ala His Gly Lys Lys Gly Pro Ile Asp Val Ser Phe Thr
145                 150                 155                 160
Asn Tyr Glu Phe Ser Gln Ser Ala Ser Trp Asn Ala Ser Leu Glu Thr
                165                 170                 175
Leu Asp Phe Thr Ala Leu Pro Asp Ile Leu Asn Gly Thr Leu Ala Gly
                180                 185                 190
Tyr Ser Thr Thr Pro Asn Ile Leu Asp Pro Glu Thr Val Gln Arg Val
            195                 200                 205
Asp Ser Tyr Thr Gly Tyr Ile Ala Pro Tyr Thr Ser Arg Asn Asn Leu
210                 215                 220
Asn Val Leu Ala Asn His Thr Val Ser Arg Ile Gln Phe Ala Pro Lys
225                 230                 235                 240
Asn Gly Ser Glu Pro Leu Lys Ala Thr Gly Val Glu Trp Tyr Pro Thr
                245                 250                 255
Gly Asn Lys Asn Gln Lys Gln Ile Ile Lys Ala Arg Tyr Glu Val Ile
            260                 265                 270
Ile Ser Ser Gly Ala Ile Gly Ser Pro Lys Leu Leu Glu Ile Ser Gly
            275                 280                 285
Ile Gly Asn Lys Asp Ile Val Ser Ala Ala Gly Val Glu Ser Leu Ile
        290                 295                 300
Asp Leu Pro Gly Val Gly Ser Asn Met Gln Asp His Val His Ala Ile
305                 310                 315                 320
Thr Val Ser Thr Thr Asn Ile Thr Gly Tyr Thr Thr Asn Ser Val Phe
                325                 330                 335
Val Asn Glu Thr Leu Ala Gln Glu Gln Arg Glu Glu Tyr Glu Ala Asn
                340                 345                 350
Lys Thr Gly Ile Trp Ala Thr Thr Pro Asn Asn Leu Gly Tyr Pro Thr
            355                 360                 365
Pro Glu Gln Leu Phe Asn Gly Thr Glu Phe Val Ser Gly Lys Glu Phe
            370                 375                 380
Ala Asp Lys Ile Arg Asn Ser Thr Asp Glu Trp Ala Asn Tyr Tyr Ala
385                 390                 395                 400
Ser Thr Asn Ala Ser Asn Val Glu Leu Leu Lys Gln Tyr Ala Ile
                405                 410                 415
Val Ala Ser Arg Tyr Glu Glu Asn Tyr Leu Ser Pro Ile Glu Ile Asn
            420                 425                 430
Phe Thr Pro Gly Tyr Glu Gly Ser Gly Asn Val Asp Leu Gln Asn Asn
            435                 440                 445
Lys Tyr Gln Thr Val Asn His Val Leu Ile Ala Pro Leu Ser Arg Gly
450                 455                 460
```

```
Tyr Thr His Ile Asn Ser Ser Asp Val Glu Asp His Ser Val Ile Asn
465                 470                 475                 480

Pro Gln Tyr Tyr Ser His Pro Met Asp Ile Asp Val His Ile Ala Ser
            485                 490                 495

Thr Lys Leu Ala Arg Glu Ile Ile Thr Ala Ser Pro Gly Leu Gly Asp
        500                 505                 510

Ile Asn Ser Gly Glu Ile Glu Pro Gly Met Asn Ile Thr Ser Glu Asp
    515                 520                 525

Asp Leu Arg Ser Trp Leu Ser Asn Asn Val Arg Ser Asp Trp His Pro
530                 535                 540

Val Gly Thr Cys Ala Met Leu Pro Lys Glu Leu Gly Val Val Ser
545                 550                 555                 560

Pro Ala Leu Met Val Tyr Gly Thr Ser Asn Leu Arg Val Val Asp Ala
                565                 570                 575

Ser Ile Met Pro Leu Glu Val Ser Ser His Leu Met Gln Pro Thr Tyr
                580                 585                 590

Gly Ile Ala Glu Lys Ala Ala Asp Ile Ile Lys Asn Phe Tyr Lys Thr
            595                 600                 605

Gln His Lys Asn Gln Asn
    610

<210> SEQ ID NO 33
<211> LENGTH: 20
<212> TYPE: PRT
<213> ORGANISM: Maackia amurensis

<400> SEQUENCE: 33

Met Lys Ile Thr Ala Ala Ile Ile Thr Val Ala Thr Ala Phe Ala Ser
1               5                   10                  15

Phe Ala Ser Ala
            20

<210> SEQ ID NO 34
<211> LENGTH: 21
<212> TYPE: PRT
<213> ORGANISM: Mucor prainii

<400> SEQUENCE: 34

Met Lys Ile Thr Ala Ala Ile Ile Thr Val Ala Thr Ala Phe Ala Ser
1               5                   10                  15

Phe Ala Ser Ala Gln
            20

<210> SEQ ID NO 35
<211> LENGTH: 27
<212> TYPE: PRT
<213> ORGANISM: Mucor prainii

<400> SEQUENCE: 35

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser
            20                  25

<210> SEQ ID NO 36
<211> LENGTH: 28
<212> TYPE: PRT
<213> ORGANISM: Mucor prainii
```

```
<400> SEQUENCE: 36

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser
            20                  25

<210> SEQ ID NO 37
<211> LENGTH: 60
<212> TYPE: PRT
<213> ORGANISM: Mucor prainii

<400> SEQUENCE: 37

Met Lys Ile Thr Ala Ala Ile Ile Thr Val Ala Thr Ala Phe Ala Ser
1               5                   10                  15

Phe Ala Ser Ala Gln Gln Asp Thr Asn Ser Ser Ser Thr Asp Thr Tyr
            20                  25                  30

Asp Tyr Val Ile Val Gly Gly Gly Val Ala Gly Leu Ala Leu Ala Ser
        35                  40                  45

Arg Ile Ser Glu Asn Lys Asp Val Thr Val Ala Val
    50                  55                  60

<210> SEQ ID NO 38
<211> LENGTH: 41
<212> TYPE: PRT
<213> ORGANISM: Mucor prainii

<400> SEQUENCE: 38

Met Gln Gln Asp Thr Asn Ser Ser Thr Asp Thr Tyr Asp Tyr Val
1               5                   10                  15

Ile Val Gly Gly Gly Val Ala Gly Leu Ala Leu Ala Ser Arg Ile Ser
            20                  25                  30

Glu Asn Lys Asp Val Thr Val Ala Val
            35                  40

<210> SEQ ID NO 39
<211> LENGTH: 40
<212> TYPE: PRT
<213> ORGANISM: Mucor prainii

<400> SEQUENCE: 39

Met Gln Asp Thr Asn Ser Ser Ser Thr Asp Tyr Asp Tyr Val Ile
1               5                   10                  15

Val Gly Gly Gly Val Ala Gly Leu Ala Leu Ala Ser Arg Ile Ser Glu
            20                  25                  30

Asn Lys Asp Val Thr Val Ala Val
            35                  40

<210> SEQ ID NO 40
<211> LENGTH: 34
<212> TYPE: PRT
<213> ORGANISM: Mucor prainii

<400> SEQUENCE: 40

Met Ser Thr Asp Thr Tyr Asp Tyr Val Ile Val Gly Gly Gly Val Ala
1               5                   10                  15

Gly Leu Ala Leu Ala Ser Arg Ile Ser Glu Asn Lys Asp Val Thr Val
            20                  25                  30

Ala Val
```

```
<210> SEQ ID NO 41
<211> LENGTH: 33
<212> TYPE: PRT
<213> ORGANISM: Mucor prainii

<400> SEQUENCE: 41

Met Thr Asp Thr Tyr Asp Tyr Val Ile Val Gly Gly Gly Val Ala Gly
1               5                   10                  15

Leu Ala Leu Ala Ser Arg Ile Ser Glu Asn Lys Asp Val Thr Val Ala
            20                  25                  30

Val
```

E. COLI TRANSFORMANT, METHOD FOR PRODUCING FLAVIN-BOUND GLUCOSE DEHYDROGENASE USING THE SAME, AND MUTANT FLAVIN-BOUND GLUCOSE DEHYDROGENASES

CROSS-REFERENCE TO RELATED APPLICATION

This application is the United States national phase application of International Application PCT/JP2011/077608 filed Nov. 30, 2011.

The contents of the electronic SEQUENCE LISTING filed on Aug. 5, 2015 (name of text file: SEQUENCE LISTING; size in bytes: 55 KB; date of creation: Aug. 5, 2015) is herein incorporated by reference in its entirety.

TECHNICAL FIELD

The invention relates to an *E. coli* transformant for the efficient recombinant production of a flavin-bound glucose dehydrogenase derived from *Mucor* in *E. coli*, a method for producing a flavin-bound glucose dehydrogenase using the same, and mutant flavin-bound glucose dehydrogenases.

BACKGROUND ART

Blood glucose levels (blood sugar levels) are an important marker of diabetes. An SMBG (self-monitoring of blood glucose) device using an electrochemical biosensor is widely used for managing blood glucose levels in patients with diabetes. Enzymes that catalyze glucose as a substrate, such as glucose oxidase (GOD), have conventionally been used for biosensors employed in SMBG devices. However, GOD is characterized by the use of oxygen as an electron acceptor. Thus, SMBG devices using GOD may influence the measurement of dissolved oxygen in a sample, precluding accurate measurement.

Other enzymes that use glucose as a substrate, but do not use oxygen as an electron acceptor include various glucose dehydrogenases (GDHs). Specifically, GDH (NAD (P)-GDH) that uses nicotinamide dinucleotide (NAD) or nicotinamide dinucleotide phosphate (NADP) as a coenzyme and GDH(PQQ-GDH) that uses pyrroloquinoline quinone (PQQ) as a coenzyme were found, and have been used for the biosensors of SMBG devices. However, NAD (P)-GDH has a problem that the enzyme is unstable and requires the addition of coenzyme. PQQ-GDH has a problem that sugar compounds other than glucose in a sample affect measurements, precluding accurate measurements, because it also reacts with sugar compounds other than glucose to be measured, such as maltose, D-galactose, and D-xylose, because of low substrate specificity.

According to a recent report, during the measurement of the blood glucose level of a patient with diabetes, who received infusion with an SMBG device using PQQ-GDH as a biosensor, PQQ-GDH also reacted with maltose contained in an infusion, raising a measured value as compared with the actual blood glucose level, and the patient developed hypoglycemia due to treatment based on this value. In addition, similar events may occur in patients who participate in a trial on galactose tolerance or xylose absorption (see, for example, Non-patent document 1). In response to this, the Pharmaceutical and Food Safety Bureau, Ministry of Health, Labour and Welfare conducted a cross-reactivity test to investigate the effects of the addition of each sugar into a glucose solution on blood glucose measurements. When maltose was added at 600 mg/dL, D-galactose at 300 mg/dL, and D-xylose at 200 mg/dL, measurements with a blood glucose measurement kit using the PQQ-GDH method were 2.5-3 times higher than the actual glucose level. Specifically, maltose, D-galactose, and D-xylose that may exist in a measurement sample preclude accurate measurement. The development of GDH that allows specific glucose measurement with high substrate specificity without being affected by sugar compounds that cause measurement errors is desired.

Under the above circumstances, GDHs using coenzymes other than those described above have attracted attention. For example, although the substrate specificity has not been described in detail, reports were published regarding a GDH derived from *Aspergillus oryzae* (see, for example, Non-patent documents 2-5). In addition, a glucose dehydrogenase using flavin adenine dinucleotide (FAD) from *Aspergillus* as a coenzyme (FAD-GDH) has been disclosed (see, for example, Patent documents 1-3). An FAD-GDH derived from *Aspergillus*, with reduced effects on D-xylose, has also been disclosed (see, for example, Patent document 4).

As described above, some FAD-GDHs having low reactivity with one or several sugar compounds other than D-glucose are known. However, no flavin-bound GDH having sufficiently low reactivity with all of maltose, D-galactose, and D-xylose is known. In addition, no flavin-bound GDH that allows accurate measurement of glucose levels in the presence of D-glucose, maltose, D-galactose, and D-xylose without being influenced by sugar compounds thereof is known. In addition, neither method nor means for efficiently producing a flavin-bound GDH having such excellent substrate specificity has been reported.

Methods for preparing a transformant by introducing an enzyme gene of interest into a suitable host and producing the enzyme by culturing the transformant is conventionally known as a means for efficiently producing a useful enzyme. Particularly, a method for introducing a gene into *E. coli* is widely used as a means for efficiently producing a substance. However, there are few findings regarding recombinant FAD-GDH production in *E. coli*. Only a method for recombinant expression by introducing an FAD-GDH gene derived from *Aspergillus* or *Penicillium* into *E. coli* $K_{12}$ strain host is disclosed (for example, see, Patent document 5).

In expressing a gene by introducing it into a host, the efficiency actually varies with genes and heterologous hosts. Of note, in introducing a gene into a heterologous host, particularly, introducing a eukaryotic gene into *E. coli*, there may often be problems with introduction or expression in the host even using a known method with reference to the findings of the same kind of enzyme. *E. coli* has no a post-translational modification system. Thus, in general, expressing the activity of an enzyme derived from a eukaryotic organism (e.g., fungi) in *E. coli* is often difficult when the enzyme activity requires post-translational modification. For example, when an enzyme derived from fungi is expressed in *E. coli*, it causes an insoluble inclusion body in most cases.

Under such circumstances, it is industrially useful to find a combination of gene, host, and introduction method, which facilitates the expression and efficient production of an enzyme, derived from a eukaryotic organism (e.g., fungi), in *E. coli*. Besides an FAD-GDH having excellent properties, a technique for efficient production of an enzyme having such excellent properties in *E. coli*, advantageous for industrial enzyme production, is strongly demanded.

PRIOR ART DOCUMENTS

Patent Documents

[Patent document 1] Japanese Patent Application Kokai Publication No. 2007-289148

[Patent document 2] WO 04/058958
[Patent document 3] WO 07/139,013
[Patent document 4] Japanese Patent Application Kokai Publication No. 2008-237210
[Patent document 5] Japanese Patent Publication No. 4561764

Non-Patent Documents

[Non-patent document 1] Pharmaceuticals and Medical Devices Safety Information No. 206, October 2004, Pharmaceutical and Food Safety Bureau, Ministry of Health, Labour and Welfare
[Non-patent document 2] Studies on the glucose dehydrogenase of *Aspergillus oryzae*. I. Induction of its synthesis by p-benzoquinone and hydroquinone, T. C. Bak, and R. Sato, Biochim. Biophys. Acta, 139, 265-276 (1967).
[Non-patent document 3] Studies on the glucose dehydrogenase of *Aspergillus oryzae*. II. Purification and physical and chemical properties, T. C. Bak, Biochim. Biophys. Acta, 139, 277-293 (1967).
[Non-patent document 4] Studies on the glucose dehydrogenase of *Aspergillus oryzae*. III. General enzymatic properties, T. C. Bak, Biochim. Biophys. Acta, 146, 317-327 (1967).
[Non-patent document 5] Studies on the glucose dehydrogenase of *Aspergillus oryzae*. IV. Histidyl residue as an active site, T. C. Bak, and R. Sato, Biochim. Biophys. Acta, 146, 328-335 (1967).

DISCLOSURE OF THE INVENTION

Problems to be Solved by the Invention

The present invention provides an *E. coli* transformant for the efficient production of a GDH that is specific for D-glucose and allows accurate measurement of D-glucose even in the presence of sugar compounds other than D-glucose, a method for producing a flavin-bound glucose dehydrogenase using the same, and mutant flavin-bound glucose dehydrogenases.

Means for Solving the Problems

To solve the problem described above, the inventors conducted intensive investigations. As a result of screening microorganisms producing a novel GDH that allows accurate measurement of glucose, the inventors found a novel GDH having GDH activity from a strain belonging to Mucoromycotina, which is specific for glucose and allows accurate measurement of glucose even in the presence of sugar compounds other than glucose.

The inventors purified this GDH and determined its properties, demonstrating that this enzyme is a novel flavin-bound GDH. The inventors actually measured D-glucose in the presence of maltose, D-galactose, or D-xylose and obtained the amino acid sequence of the novel GDH and the gene sequence information encoding the same. In addition, to solve the problem that it is difficult to obtain an enzyme in a sufficient amount from the culture of an original microorganism, the inventors conceived and intensively investigated the introduction of the gene into homogeneous and heterologous microorganisms. As a part of the efforts, for example, the inventors tried to prepare a transformant using a microorganism (*Aspergillus sojae*) of genus *Aspergillus* belonging to the same fungi as a host. However, most GDHs obtained using this method are produced in cells and, therefore, require the same time and labor for enzyme extraction as those produced in microorganisms of origin. In addition, no significant improvement could be achieved in view of shortening culture time, as compared with culturing an original microorganism, because *Mucor* also belongs to fungi.

Thus, the inventors obtained a transformant by introducing a gene encoding a flavin-bound GDH derived from *Mucor* into *E. coli* as a candidate host, which is advantageous in terms of shortening culture time and facilitating cell homogenization, and cultured the *E. coli* transformant to obtain a flavin-bound GDH from this culture. However, the novel GDH found by the inventors was expressed at a very low level when its full-length gene was introduced into *E. coli*.

Thus, as a result of further investigation to solve the problem, the inventors prepared a gene encoding a mutant flavin-bound glucose dehydrogenase with an amino acid sequence corresponding to MKITAAIITVATAFASFASA (SEQ ID NO: 33) that exists in the N-terminal region of the GDH deleted, and introduced this gene into a suitable vector and transformed *E. coli* using this vector to obtain an *E. coli* transformant. Then, a larger amount of a flavin-bound GDH could be efficiently obtained by culturing the *E. coli* transformant and collecting a mutant flavin-bound GDH, with its N terminus deleted, from the culture, thereby completing the invention.

Specifically, the invention relates to:

(1) an *E. coli* transformant obtained by introducing into *Escherichia coli* a gene encoding a mutant flavin-bound glucose dehydrogenase lacking the N-terminal region, comprising an amino acid sequence corresponding to MKITAAIITVATAFASFASA (SEQ ID NO: 33) that exists in the N-terminal region, from the amino acid sequence of a wild-type flavin-bound glucose dehydrogenase derived from a microorganism classified as Mucoromycotina, preferably Mucoromycetes, more preferably Mucorales, further preferably Mucoraceae;

(2) an *E. coli* transformant obtained by introducing into *Escherichia coli* a gene encoding a mutant flavin-bound glucose dehydrogenase lacking the N-terminal region, comprising an amino acid sequence corresponding to MKITAAIITVATAFASFASA (SEQ ID NO: 33)that exists in the N-terminal region, from the amino acid sequence of a flavin-bound glucose dehydrogenase, consisting of the amino acid sequence of SEQ ID NO: 1 or 3, an amino acid sequence at least 85% identical to said amino acid sequence, or an amino acid sequence having one or several amino acids deleted, substituted, or added in said amino acid sequence;

(3) a method for producing a flavin-bound glucose dehydrogenase, characterized by culturing the *E. coli* transformant of the above (1) or (2) and collecting a flavin-bound GDH from said culture; and (4) a flavin-bound glucose dehydrogenase lacking the N-terminal region, comprising an amino acid sequence corresponding to MKITAAIITVATAFASFASA (SEQ ID NO: 34) that exists in the N-terminal region, from the amino acid sequence of a flavin-bound GDH, consisting of the amino acid sequence of SEQ ID NO: 1 or 3, an amino acid sequence at least 85% identical to said amino acid sequence, or an amino acid sequence having one or several amino acids deleted, substituted, or added in said amino acid sequence.

Effect of the Invention

The *E. coli* transformant of the invention and a method for producing a flavin-bound GDH using the same allow the efficient production of a novel GDH that allows accurate measurement of glucose. Specifically, a flavin-bound GDH that allows accurate measurement of D-glucose could be efficiently obtained without being influenced by sugar compounds contained in a measurement sample, such as maltose, D-galactose, and D-xylose. Thus, a practical GDH that allows accurate measurement of blood glucose levels in samples from patients receiving a infusion containing maltose or undergoing in a galactose torerance test or xylose absorption test can be efficiently provided.

BRIEF DESCRIPTION OF THE DRAWINGS

[FIG. 8] Predicted signal peptide cleavage site of any one of the flavin-bound GDHs used in the invention.
[FIG. 9] N-terminal amino acid sequence of any one of the flavin-bound GDHs lacking a signal peptide, used in the invention.

Figure 1:
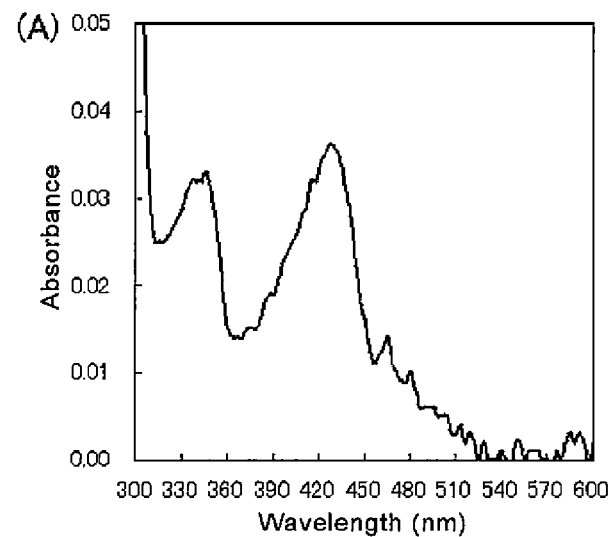
[FIG. 1] Absorption spectra of any one of the flavin-bound GDHs used in the invention.
Figure 1:
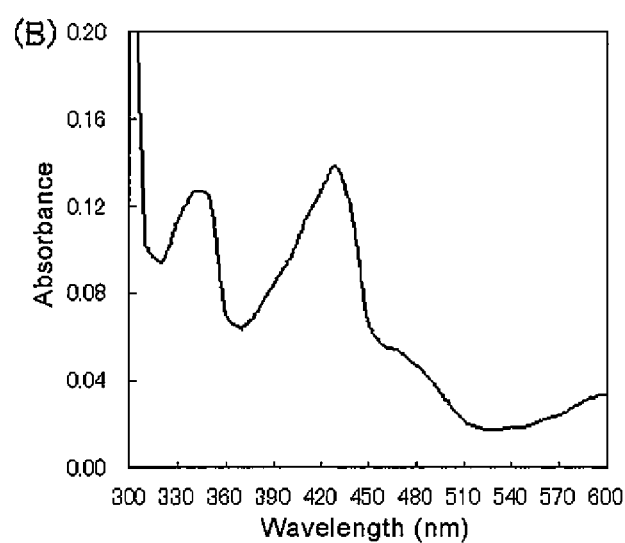
Figure 1:
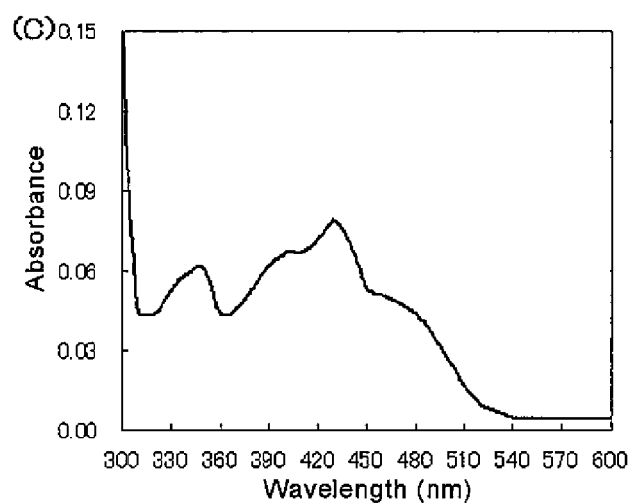

BEST MODE FOR CARRYING OUT THE INVENTION (Flavin-bound GDH)

The flavin-bound GDHs used in the invention can be obtained from a microorganism classified as Mucoromycotina, preferably Mucoromycetes, more preferably Mucorales, further preferably Mucoraceae. Microorganisms classified as Mucoromycotina, preferably Mucoromycetes, more preferably Mucorales, further preferably Mucoraceae include, for example, *Mucor*, *Absidia*, and *Actinomucor*. Specific examples of preferred microorganisms which are classified as *Mucor* and produce the flavin-bound GDHs used in the invention include *Mucor prainii*, *Mucor javanicus*, and *Mucor circinelloides* f. *circinelloides*. Specifically, they include *Mucor prainii* NISL0103, *Mucor javanicus* NISL0111, and *Mucor circinelloides* f. circinelloides NISL0117. Specific examples of preferred microorganisms which are classified as *Absidia* and produce the flavin-bound GDHs used in the invention include *Absidia cylindrospora* and *Absidia hyalospora*. Specifically, they include *Absidia cylindrospora* NISL0211 and *Absidia hyalospora* NISL0218. Specific examples of preferred microorganisms which are classified as *Actinomucor* and produce the flavin-bound GDHs used in the invention include *Actinomucor elegans*. Specifically, they include *Actinomucor elegans* NISL9082. The above strains are stored at the Noda Institute for Scientific Research (NISL) and are available through prescribed procedures.

As described above, the flavin-bound GDHs used in the invention are those that derive from a microorganism classified as Mucoromycotina, preferably Mucoromycetes, more preferably Mucorales, further preferably Mucoraceae and have the various properties described above. Furthermore, a recombinant flavin-bound GDH produced by using a gene encoding a flavin-bound GDH obtained by a known genetic engineering technique from the flavin-bound GDH-producing microorganism, partially modifying it as needed, and introducing it into a suitable host microorganism by known various techniques is also included in the flavin-bound GDHs that derive from a microorganism classified as Mucoromycotina, preferably Mucoromycetes, more preferably Mucorales, further preferably Mucoraceae and have various properties described above, used in the invention. Similarly, regarding flavin-bound GDHs that derive from a microorganism classified as *Mucor* or are described with the strain name of a specific producer microorganism, flavin-bound GDHs that are obtained based on genetic information from each microorganism and have various properties described above are also included in the invention.

(Substrate Specificity of Flavin-Bound GDHs)

The flavin-bound GDHs used in the invention were found by the inventors and characterized by excellent substrate specificity and high selectivity for D-glucose. Specifically, the flavin-bound GDHs used in the invention are poorly reactive to maltose, D-galactose, and D-xylose. Specifically, the flavin-bound GDHs used in the invention are characterized in that the reactivity to maltose, D-galactose, and D-xylose is less than 2% relative to 100% for reactivity to D-glucose. The flavin-bound GDHs used in the invention have such high substrate specificity. Thus, D-glucose can be accurately measured in samples from patients receiving a infusion containing maltose or undergoing in a galactose tolerance test load or xylose absorption test without being influenced by sugar compounds contained in a measurement sample, such as maltose, D-galactose, and D-xylose As described above, the flavin-bound GDHs used in the invention is characterized in that measurements obtained using sugar compounds, such as maltose, D-galactose, and D-xylose, instead of D-glucose, as substrates are very low and that glucose levels can be accurately measured even in the presence of contaminating sugar compounds, such as maltose, D-galactose, and D-xylose. Specifically, measurements obtained in the presence of one or several contaminating sugar compounds selected from maltose, D-galactose, and D-xylose are 96-103% and those obtained in the presence of all the contaminating sugar compounds, maltose, D-galactose, and D-xylose, are 96-104% relative to 100% for reactivity to D-glucose in the absence of these contaminating sugar compounds even in the presence of all the three compounds, maltose, D-galactose, and D-xylose. Use of the flavin-bound GDHs having such properties preferably allows accurate measurement of glucose levels even in the presence of maltose, D-galactose, and D-xylose in a measurement sample.

(Enzymatic Properties of the Flavin-Bound GDHs Used in the Invention)

Exemplary enzymes preferred as the flavin-bound GDHs used in the invention include those having the following enzymatic properties:

(1) action: GDH activity in the presence of an electron acceptor;
(2) molecular weight: approximately 80 kDa molecular weight of the polypeptide chain of the protein;
(3) substrate specificity: lower reactivity to maltose, D-galactose, and D-xylose than that to D-glucose;
(4) optimum pH: pH 6.5-7.0;
(5) optimum temperature: 37-40° C.;
(6) stable pH range: pH 3.5-7.0
(7) thermal stability: 80% or above residual activity after heat treatment at 40° C. for 15 minutes;
(8) use of flavin compound as a coenzyme; and
(9) Km value: Km value for D-glucose is 26-33 mM.

GDHs having the above enzymatic properties allow accurate measurement of D-glucose without being influenced by sugar compounds contained in a measurement sample, such as maltose, D-galactose, and D-xylose. In addition, the GDHs can be preferably used as measurement reagents for diagnoses, because they act at pH and temperature ranges preferred for applications to clinical diagnoses, such as measurement of blood glucose levels.

Although the above parameters of properties are typical examples, they may vary in an acceptable range that allows achievement of the effects of the invention in measuring D-glucose levels under predetermined measurement conditions. For example, the parameters, such as stable and optimum pH ranges and optimum temperature range, may be slightly wider than the above typical ranges within a range including the predetermined measurement conditions. On the contrary, the parameters may be slightly narrower than the above typical ranges as far as sufficient activity and/or stability are ensured under the measurement conditions. Substrate specificity is generally higher at a smaller Km value. The enzyme of the invention may have a value within a range that substantially realizes satisfactory substrate selection under the predetermined conditions.

The above various enzymatic properties can be examined using known techniques to specify various enzymatic properties, for example, methods described in the Examples below. The various enzymatic properties can be examined to some extent using a culture medium of the flavin-bound GDH-producing microorganism used in the invention during the intermediate step of a purification process and can be examined in detail using a purified enzyme.

The purified enzyme is an enzyme isolated substantially free of components other than said enzyme, particularly, free of proteins (contaminating proteins) other than said enzyme. Specifically, for example, the content of contaminating proteins on a weight basis is less than about 20%, preferably less than about 10%, more preferably less than about 5%, even more preferably less than about 1% of the total. MpGDH, MjGDH, and McGDH described herein below are purified enzymes, unless otherwise stated.

Electron acceptors utilized by the flavin-bound GDHs used in the invention are, but not particularly limited to, for example, any electron acceptor known as a preferred reagent component used for the measurement of blood glucose levels.

Coenzymes utilized by the flavin-bound GDHs used in the invention are characterized by being flavin compounds. Flavin compounds include, for example, flavin adenine dinucleotide (FAD) and flavin mononucleotide (FMN).

Exemplary enzymes preferred as the flavin-bound GDHs used in the invention include flavin-bound GDHs with approximately 80 kDa molecular weight of the polypeptide chain of the protein as measured by SDS-polyacrylamide gel electrophoresis. The flavin-bound GDHs used in the invention may be glycosylated.

Thus, without deglycosylation, their molecular weights tend to be larger than their actual values as measured by SDS-polyacrylamide gel electrophoresis.

Exemplary enzymes preferred as the flavin-bound GDHs used in the invention include those with Km values for D-glucose ranging from 26 to 33 mM.

(Action Principle and Activity Assay of the Flavin-Bound GDHs)

The flavin-bound GDHs used in the invention catalyze a reaction for generating glucono-δ-lactone by oxidizing the hydroxyl group of glucose in the presence of an electron acceptor.

Thus, this principle can be employed, for example, to measure the flavin-bound GDHs used in the invention with the measurement system described below using phenazine methosulfate (PMS) and 2,6-dichloro-indophenol (DCIP) as electron acceptors.

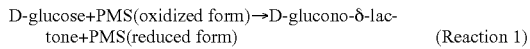
D-glucose+PMS(oxidized form)→D-glucono-δ-lactone+PMS(reduced form)　　　(Reaction 1)

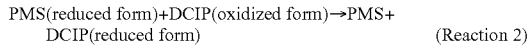
PMS(reduced form)+DCIP(oxidized form)→PMS+DCIP(reduced form)　　　(Reaction 2)

First, in the reaction 1, PMS (reduced form) is generated along with glucose oxidization. In the subsequent reaction 2, DCIP is reduced along with PMS oxidation, allowing measurement of disappeared oxidized DCIP from the amount of change in absorbance at 600-nm wavelength.

Specifically, the activities of the flavin-bound GDHs are measured according to the following procedures. To initiate a reaction, 1.79 mL of 100 mM phosphate buffer (pH7.0), 0.08 mL of 1.25 M D-glucose solution, and 0.01 mL of 20 mM DCIP solution are mixed, followed by incubation at 37° C. for 5 minutes, and, subsequently, 0.02 mL of 20 mM PMS solution and 0.1 mL of an enzyme sample solution are added. Absorbance is measured at the initiation of the reaction and over time to determine a decrease in the absorbance at 600 nm (ΔA600) per minute due to the progress of the enzyme reaction and calculate flavin-bound GDH activity according to the following formula. At that time, one unit of the flavin-bound GDH activity is defined as the amount of an enzyme that reduces 1 μmol of DCIP at 37° C. within one minute in the presence of 50 mM D-glucose.

$$GDH \text{ activity } (U/\text{ml}) = \frac{-(\Delta A600 - \Delta A600_{blank}) \times 2.0 \times df}{16.3 \times 0.1 \times 1.0} \quad \text{[Formula 1]}$$

The formula indicates 2.0 as the liquid volume (mL) of reaction reagent plus enzyme reagent, 16.3 as millimolar extinction coefficient (cm$^2$/μmol) under the activity assay conditions, 0.1 as the liquid volume (mL) of an enzyme solution, 1.0 as the optical path length (cm) of a cell, $\Delta A600_{blank}$ as a decrease in the absorbance at 600 nm per minute when 10 mM acetate buffer, instead of an enzyme sample solution, is added to initiate a reaction, and df as a dilution factor.

(Amino Acid Sequences of Flavin-Bound GDHs)

The flavin-bound GDHs used in the invention is characterized by having the amino acid sequence of SEQ ID NO: 1 or 3, an amino acid sequence at least 85% identical to said amino acid sequence, or an amino acid sequence having one or several amino acids deleted, substituted, or added in said amino acid sequence. The flavin-bound GDH having the amino acid sequence of SEQ ID NO: 1 or 3 have the above various properties. In addition, GDHs having an amino acid sequence at least 85%, preferably 90%, most preferably 95% or above identical to the amino acid sequence of SEQ ID NO: 1 or 3 and having the same various properties as the flavin-bound GDH having the amino acid sequence of SEQ ID NO: 1 or 3 are also included in the flavin-bound GDHs of the invention.

(Gene Sequences Encoding Flavin-Bound GDHs)

The genes encoding the flavin-bound GDHs used in the invention refer to DNAs encoding flavin-bound GDHs having the amino acid sequence of SEQ ID NO: 1 or 3, an amino acid sequence at least 85% identical to said amino acid sequence, or an amino acid sequence having one or several amino acids deleted, substituted, or added in said amino acid sequence.

The genes encoding the flavin-bound GDHs used in the invention refer to DNAs consisting of a base sequence of SEQ ID NO: 2 or 4. Alternatively, the genes encoding the flavin-bound GDHs used in the invention refer to DNAs having an base sequence at least 85%, preferably 90%, most preferably 95% or above identical to the base sequence of SEQ ID NO: 2 or 4 and encoding proteins having flavin-bound GDH enzyme activity.

(Vectors Containing Gene Sequences Encoding Flavin-Bound GDHs and Transformants)

The genes encoding the flavin-bound GDHs used in the invention may be inserted into known various suitable vectors. Furthermore, these vectors may be introduced into known various suitable hosts to generate transformants with recombinant DNAs containing flavin-bound GDH genes introduced. Methods for obtaining these genes, gene sequences, and amino acid sequence information and generating various vectors and transformants are known to those skilled in the art. Some examples are described below.

A routine gene cloning methods is employed to obtain a flavin-bound GDH gene from a flavin-bound GDH-producing microorganism. For example, chromosomal DNA or mRNA can be extracted from microorganisms and cells with a flavin-bound GDH-producing ability using routine methods, such as those described in Current Protocols in Molecular Biology (WILEY Interscience, 1989). Furthermore, cDNA can be synthesized using mRNA as a template. The above chromosomal DNA or cDNA can be used to generate a chromosomal DNA or cDNA library.

Subsequently, an appropriate DNA probe is synthesized based on the amino acid sequence of a flavin-bound GDH. This probe is used to screen a chromosomal DNA or cDNA library. Alternatively, appropriate DNA primers are generated based on the above amino acid sequences to amplify DNA fragments containing gene fragments of interest using polymerase chain reaction (PCR), such as 5' or 3' RACE method. The DNA fragments, thus obtained, can be ligated to obtain a DNA fragment containing a full-length gene of interest.

Preferred examples of the genes encoding flavin-bound GDHs, thus obtained, include a flavin-bound GDH gene derived from *Mucor*. These genes are preferably ligated to various vectors using routine methods to facilitate handling. For example, a recombinant plasmid containing an isolated gene encoding a flavin-bound GDH derived from *Mucor* is generated. The gene can be extracted and purified from the plasmid using, for example, QIAGEN (QIAGEN). DNA vectors that can be used in the invention include, for example, DNA plasmid and bacteriophage vectors. Specifically, for example, pBluescriptII SK+ (STRATAGENE) is preferred.

The base sequence of the flavin-bound GDH gene, obtained by the above method, may be determined and confirmed using, for example, multi-capillary DNA analysis system CEQ2000 (Beckman Coulter, Inc.).

The resulting flavin-bound GDH gene can be inserted into an appropriate vector by a routine method, as described below, to transform or be introduced into hosts corresponding to each vector by a routine method. Specifically, for example, the flavin-bound GDH gene can be ligated to an appropriate vector to obtain a recombinant vector. Any vector that may produce a flavin-bound GDH in a host to be transformed can be used. For examples, plasmid, cosmid, phage, virus, chromosomally integrated, and artificial chromosome vectors can be used. If a plasmid is used as a vector, pBluescript, pUC18, pET-22b (+), and pET-16b, for example, can be used when *Escherichia coli* is used as a host microorganism.

The above vector may contain a marker gene that allows selection of transformed cells. Marker genes include, for example, genes that complement host auxotrophy, such as URA3 and niaD, or genes that confer resistance to agents, such as ampicillin, kanamycin, and oligomycin. Recombinant vectors desirably contain a promoter that facilitates the expression of the gene of the invention in host cells or other regulatory sequences (e.g., enhancer, terminator, and polyadenylation sequences). Specifically, promoters include, for example, GAL1, amyB, and lac promoters. A tag for purification may be used. For example, a linker sequence is appropriately connected downstream of a flavin-bound GDH gene, and a base sequence encoding six or more codons of histidine is connected, allowing purification using a nickel column.

(Hosts Used for the Transformant of the Invention)

The transformant of the invention can be obtained by transforming a host microorganism with the above recombinant vector. Exemplary hosts used for the transformant of the invention include microorganisms belonging to *Escherichia coli*. Specifically, preferred microorganisms classified as *Escherichia coli* include *Escherichia coli* W3110, BL21 (DE3), YM109, and DH5a. These strains are commercially available.

(Transformation)

*Escherichia coli* can be transformed by a known method for the host. For host microorganisms belonging to *Escherichia*, a method for introducing recombinant DNA in the presence of calcium ions may be employed, or electroporation may be used (Methods Enzymol., 194, 182-187 (1990)). Furthermore, although commercial competent cells (e.g., ECOS BL21 (DE3); Nippon Gene Co., Ltd.) may be used, any method may be employed for transformation without limitation.

(Deletion of an N-Terminal Peptide)

The *E. coli* transformant of the invention and a method for producing an FAD-GDH using the same are characterized in that a mutant GDH gene with a peptide sequence of a certain length, which exists at the N terminus, deleted is introduced into *E. coli* for the recombinant expression of FAD-GDH. This can markedly increase enzyme productivity as compared with the introduction of a wild-type GDH gene with the peptide sequence undeleted and/or the production of GDH in the culture of the original microorganism.

The FAD-GDH derived from *Mucor*, used in the invention, is a novel enzyme of practical use. Its amino acid and gene sequences were unknown. Thus, unsurprisingly, besides recombinant production, efficient production for expression in a heterologous host was not considered at all. In fact, the amino acid and gene sequences elucidated after the inventors found an FAD-GDH derived from *Mucor* have an extremely low homology with those of conventionally known FAD-GDHs. Specifically, regarding the efficient recombinant production of the FAD-GDH used in the invention, difficulties of referring to and applying the findings of other FAD-GDHs with significantly different origins and structures were strongly suggested, demanding individual trials and errors.

(Prediction of the Deletion Region of an N-Terminal Peptide)

The prediction of a signal peptide is an effective means for determining an N-terminal deletion region, which contributes to the efficient recombinant production of the FAD-GDH used in the invention. A signal peptide exists as an extended peptide of 15-30 residues at the N terminus of a mature protein. A region of hydrophobic amino acids exists in the signal peptide sequence, facilitating a nascent polypeptide chain to attach to and pass through the endoplasmic reticulum membrane. After passing through the membrane, the signal peptide is cleaved. Specifically, a signal peptide is used for intracellular transport and is cleaved after the transport. Thus, the signal peptide region of GDH is not involved in GDH activity. Thus, deletion within a signal peptide region is unlikely to impair enzyme activity.

In addition, when the FAD-GDH derived from *Mucor*, used in the invention, is heterologously expressed in an *E. coli* host, a signal peptide has no transport function in the strain of origin and exists with a hydrophobic peptide chain added in an *E. coli* strain, suggesting the possibility of reducing expression levels, such as lowering the stability of GDH. Hence, the length of a signal peptide is predicted using a suitable tool. A mutant GDH gene with its N terminus deleted in the vicinity of the signal peptide is generated to be introduced into *E. coli* to compare enzyme expressions, providing an effective means for determining an N-terminal deletion region of a suitable length. Such signal peptide prediction tools include, for example, a signal peptide prediction program available from the web (SignalP, www.cbs.dtu.dk/services/SignalP-2.0/).

(Deletion Region of the N-Terminal Peptide of GDH in the Invention)

The *E. coli* transformant of the invention and a method for producing an FAD-GDH using the same can increase expression levels when expressed in *E. coli* by deleting the N-terminal region containing a region corresponding to the signal peptide that exists in the N-terminal region of the GDH derived from *Mucor*. Specifically, for example, a signal peptide can be deleted in GDHs having the amino acid sequence of SEQ ID NO: 1 or 3 when expressed after deleting DNA encoding the N-terminal region containing the amino acid sequence MKITAAIITVATAFASFASA (SEQ ID NO: 33)that exists at the N terminus. Deleting the region can markedly increase the expression and/or production of the GDH produced in the *E. coli* transformant of the invention.

The "amino acid sequence MKITAAIITVATAFASFASA (SEQ ID NO: 33) that exists at the N terminus" of the invention refers to an amino acid sequence in a GDH having a certain homology (e.g., 85%, preferably 90%, more preferably 95% or above identity) with a GDH having the amino acid sequence of SEQ ID NO: 1 or 3. The relationship of corresponding positions and sequences between these GDHs having an amino acid sequence identity above a certain level can be readily revealed by comparing the amino acid sequences of various GDHs and the GDH of SEQ ID NO: 1 or 3 using commercial amino acid homology analysis software, for example, GENETYX-Mac (Software Development).

No other GDH highly homologous to the GDH derived from *Mucor*, found by the inventors, has been reported. However, in general, mutually homologous enzyme proteins are likely to be similar in their protein structures in highly homologous regions. Thus, the relationship of corresponding amino acid sequences is often analyzed by the homology analysis of multiple enzymes having an amino acid sequence identity above a certain level, in order to introduce similar mutation or deletion into a certain amino acid position or its corresponding amino acid position in an amino acid sequence region to confer the same effects on enzyme properties. Thus, the findings of the invention about the deletion region of the N-terminal peptide of the GDH of the invention, illustrated by SEQ ID NO: 1 or 3, are also utilized for GDHs, facilitating the deletion of a similar amino acid sequence in the corresponding regions of other GDHs in order to achieve the same effects for these GDHs.

The deletion region of the N-terminal peptide of the GDH of the invention is not necessarily a signal peptide region alone. For example, besides deleting the N-terminal signal peptide alone, the signal peptide region or its adjacent region, containing a region that has no adverse effects on enzyme activity, may be deleted. Specifically, for example, in the GDH having the amino acid sequence of SEQ ID NO: 3, MKITAAIITVATAFASFASA (SEQ ID NO: 33) that exists at the N terminus may be deleted, or, MKITAAIITVATAFAS-FASAQ, (SEQ ID NO: 34) which deletes a single additional residue, may be deleted. More residues may be deleted as far as the deletion has no adverse effects on enzyme activity. For example, in the GDH having the amino acid sequence of SEQ ID NO: 3, MKITAAIITVATAFASFASAQQDTNSS (SEQ ID NO: 35) that exists at the N terminus may be deleted, or, MKITAAIITVATAFASFASAQQDTNSSS (SEQ ID NO: 36), which deletes a single additional residue, may be deleted. Substantial deletion of the N-terminal signal peptide region is important for the invention. Deletion of an additional region, along with the N-terminal signal peptide region, is not essential for the invention. Variable deletions of multiple N-terminal regions are included in the GDH of the invention as far as the same effects can be achieved. Depending on the origins and hosts of GDH, even if a short N-terminal region (e.g., one or several residues) is deleted from the N-terminal signal peptide region, no substantial difference is observed between the effects of this deletion and those of the deletion of the entire N-terminal signal peptide region or the deletion of a longer N-terminal region containing the entire N-terminal signal peptide region. Such deletions are also included in the variable deletions of the invention.

Methods for deleting the N-terminal peptide include, but are not limited to, known means, for example, a method for altering the N-terminal amino acid, generated by signal peptide cleavage, to a start codon, methionine. Alternatively, adding a start codon, methionine, to the N-terminal amino acid generated by signal peptide cleavage allows the expression of a signal peptide-deleted GDH in *E. coli*. Alternatively, as described above, to delete a peptide containing the signal peptide and its small adjacent region, a method for expression with the N-terminal amino acid, generated by the cleavage of the predicted region, altered to a start codon, methionine, or a method for addition of a start codon, methionine, to the N-terminal amino acid generated by cleavage are also considered.

Depending on a procedure, i.e., replacing the new N terminus, generated by cleavage of a certain N-terminal region by methionine or adding methionine without replacement, the resulting amino acid sequence of GDH differ by one residue. This is a procedure for adding a start codon, methionine, when the new N terminus generated by deleting the signal peptide is not methionine, in order to provide a start codon to facilitate the expression of a normal protein from the gene, and is not essential for the invention.

An increase in the expression of the enzyme of interest, as compared with expression in the presence of a signal peptide sequence, can be demonstrated by comparing the total activities in 1 mL of culture medium before and after introducing a mutation into the sequence. The deletion of the signal peptide can also be confirmed by N-terminal amino acid sequencing using Edman degradation. PSORT and SignalP are commonly used as signal peptide prediction programs. These are available from the web addresses: psort.nibb.ac.jp/ and www.cbs.dtu.dk/services/SignalP-2.0/.

(Production of a Flavin-Bound GDH)

The *E. coli* transformant obtained by the above transformation is used to produce a flavin-bound GDH. Specifically, the *E. coli* transformant obtained by the above transformation is cultured to obtain a flavin-bound glucose dehydrogenase from the culture.

A technique for producing a certain useful protein by introducing the gene encoding the protein into a heterologous host is theoretically known. However, in fact, its effectiveness varies with the kinds of genes and heterologous hosts, used for introduction. Often, a gene cannot be introduced into or expressed in a heterologous host. Specifically, it is difficult to find a combination of gene, host, and introduction method to facilitate the production of substances. Thus, it is industrially useful to find a combination of gene, host, and introduction method to achieve efficient production.

Significantly more efficient enzyme production can be achieved by culturing the transformant of the invention than by culturing the microorganism (i.e., *Mucor*), from which the flavin-bound GDH used in the invention derives from. Specifically, a larger amount of an enzyme can be produced. The flavin-bound GDH derived from *Mucor*, used in the invention, cannot produce a sufficient amount of flavin-bound GDH in the culture of the original microorganism, requiring a larger scale of fungal culture. In addition, the culture requires 3-5 days, and processes of collecting the cultured cells by centrifugation, homogenizing the mycelia (enzyme extraction), and preparing a crude enzyme solution by second centrifugation are required. The use of the transformant (i.e., *E. coli*) of the invention can shorten the culture period and markedly facilitate the bacterial homogenization (enzyme extraction) process, allowing efficient production.

(Culture of *E. coli* Transformant)

The *E. coli* transformant of the invention may be cultured by routine solid culture and preferably by liquid culture wherever possible. Any media containing carbon and nitrogen sources, inorganic substances, and other nutrients as needed may be used. Both synthetic and natural media may be used. Any media that allow efficient production of an enzyme of interest may be used.

Assimilable carbon compounds (e.g., glucose, starch hydrolyzate, glycerin, fructose, and molasses) may be used as carbon sources used in media. Available nitrogen compounds (e.g., yeast extract, peptone, meat extract, corn steep liquor, soy flour, malt extract, amino acids, ammonium sulfate, and ammonium nitrate) may be used as nitrogen sources. Inorganic substances include, for example, various salts, such as sodium chloride, potassium chloride, magnesium sulfate, manganese chloride, ferrous sulfate, monopotassium phosphate, dipotassium phosphate, sodium carbonate, and calcium chloride. In addition, vitamins and antifoaming agents may be added as needed.

In addition, nutrient sources or components, which can increase the production of the flavin-bound GDH used in the invention when added, may be used alone or in combination.

Culture conditions may vary with microorganisms to be cultured. For example, the initial pH of medium may be adjusted to 5-10, culture temperature to 20-40° C., culture time to 15-25 hours, 1-2 days, or 10-50 hours as needed. Any culture methods, such as aeration-agitation submerged culture, shaking culture, and static culture, may be employed. One example of medium to culture microorganisms (e.g., *E. coli*) and culture conditions is shaking culture at 120 rpm at 25° C. for four days in a medium of 0.1% yeast extract, 0.1% malt extract, 0.1% potassium dihydrogen phosphate, 0.05% magnesium sulfate, and pH 7.3. An additional example of culture conditions for the *E. coli* transformant of the invention is shaking culture at 37° C. for four hours after inoculation in 10 mL of TY medium (1% Bacto-tryptone, 0.5% Bacto-yeast extract, 0.5% NaCl, pH 7.0) containing 100 μg/mL ampicillin and 1 mM IPTG, followed by additional shaking culture at 20° C. overnight. Optimizing culture conditions depending on transformants to be used shortens culture time and increases enzyme production, contributing to efficient enzyme production.

After the completion of the culture, routine procedures for enzyme collection may be employed to collect a flavin-bound GDH from the culture or the cultured bacteria. If the enzyme exists in bacteria, the bacteria are preferably separated by procedures, such as filtration and centrifugation, to collect the enzyme from the bacteria. For example, methods for crushing bacteria using routine procedures, such as sonicator, French press, and Dyno-Mill, and methods for lysing bacterial wall using cell wall lytic enzymes, such as lysozyme, and methods for extracting enzyme from bacteria using surfactants, such as Triton X-100, can be employed alone or in combination.

Subsequently, insolubles are removed by filtration or centrifugation to obtain an enzyme extract. To isolate and purify a flavin-bound GDH from the obtained extract as needed, nucleic acid is removed as needed, and ammonium sulfate, alcohol, and acetone are added, followed by fractionation to obtain a precipitate. To obtain an enzyme preparation of higher purity, gel filtration using Sephadex, Ultra gel, or Bio-Gel, adsorption elution using ion exchanger or hydroxyapatite, affinity chromatography, fractionation using a molecular sieve or hollow fiber membrane, for example, are appropriately selected or combined.

The flavin-bound GDH used in the invention may be modified in its gene and amino acid sequence through partial deletion, substitution, addition, and/or insertion using known gene engineering techniques. Such flavin-bound GDHs to which desired properties are conferred can also be efficiently produced using the *E. coli* transformant of the invention.

The flavin-bound GDHs produced as described above allow accurate measurement of glucose levels even in the presence of contaminating sugar compounds and, therefore, can be preferably applied to glucose sensors.

Hereinafter, the invention is more specifically described with Examples. However, they are not intended to limit the scope of the invention.

EXAMPLE 1

(Acquisition of a Flavin-Bound GDH Derived from *Mucor*)
1. Screening of GDH-Producing Cells Strains isolated from natural environments and about 500 stored strains supplied by a culture collection institution (Noda Institute for Scientific Research) were screened for GDH production. Each bacterial strain under test was inoculated into 3 mL of malt extract medium (2.0% malt extract, 2.0% D-glucose, 0.1% polypeptone, pH 6.0), followed by shaking culture at 30° C. for 3-5 days. The culture medium was centrifuged at 800×g for 10 minutes to precipitate cells. Subsequently, the cells were suspended in 10 mM acetate buffer (pH 5.0) and homogenized using a Multi-beads Shocker (Yasui Kikai) (2,000 rpm, 60 seconds, 16 times). The supernatant collected by centrifugation at 20,000×g and 4° C. for 10 minutes was used as a crude enzyme solution.

2. Determination of GDH Activity

Solutions were mixed according to the following procedures, followed by absorbance measurement to examine GDH activity in the crude enzyme solution. To initiate a reaction, 1.79 mL of 100 mM phosphate buffer (pH 7.0), 0.08 mL of 1.25 M D-glucose solution, and 0.01 mL of 20 mM DCIP solution were mixed, followed by incubation at 37° C. for five minutes, and 0.02 mL of 20 mM PMS solution and 0.1 mL of an enzyme sample solution were added. A decrease in the absorbance at 600 nm ($\Delta A600$) per minute due to the progress of the enzyme reaction after the initiation of the reaction was determined to calculate GDH activity according to the following formula. At that time, one unit of GDH activity is defined as the amount of an enzyme that reduces 1 μmol of DCIP at 37° C. within one minute in the presence of 50 mM D-glucose.

$$GDH \text{ activity } (U/\text{ml}) = \frac{-(\Delta A600 - \Delta A600_{blank}) \times 2.0 \times df}{16.3 \times 0.1 \times 1.0}$$ [Formula 2]

The formula indicates 2.0 as the liquid volume (mL) of reaction reagent plus enzyme reagent, 16.3 as millimolar extinction coefficient (cm$^2$/μmol) under the activity assay conditions, 0.1 as the liquid volume (mL) of an enzyme solution, 1.0 as the optical path length (cm) of a cell, $\Delta A600_{blank}$ as a decrease in the absorbance at 600 nm per minute when 10 mM acetate buffer, instead of an enzyme sample solution, is added to initiate a reaction, and df as a dilution factor.

The presence or absence of GDH activity was investigated in the crude enzyme solutions from each strain according to the above activity assay. Table 1 shows the results.

TABLE 1

GDH activity detected in the crude enzyme solution

| Strain | Activity (U/mL) |
| --- | --- |
| Mucor prainii NISL0103 | 0.187 |
| Mucor javanicus NISL0107 | 0.476 |
| Mucor javanicus NISL0108 | 0.023 |
| Mucor javanicus NISL0111 | 0.714 |
| Mucor javanicus NISL0112 | 0.282 |
| Mucor javanicus NISL0115 | 0.116 |
| Mucor circinelloides f. circinelloides NISL0116 | 0.033 |
| Mucor circinelloides f. circinelloides NISL0117 | 0.136 |
| Mucor hiemalis f. silvaticus NISL0118 | 0.001 |
| Absidia cylindrospora NISL0211 | 0.007 |
| Absidia hyalospora NISL0218 | 0.006 |
| ActinoMucor elegans NISL9082 | 0.012 |

As a result, GDH activity was detected in the crude enzyme solutions derived from Mucor prainii NISL0103, Mucor javanicus NISL0107, Mucor javanicus NISL0108, Mucor javanicus NISL0111, Mucor javanicus NISL0112, Mucor javanicus NISL0115, Mucor circinelloides f. circinelloides NISLOI 16, Mucor circinelloides f. circinelloides NISL0117, Mucor hiemalis f. silvaticus NISL0118, Absidia cylindrospora NISL0211, Absidia hyalospora NISL0218, and ActinoMucor elegans NISL9082.

EXAMPLE 2

(Purification of a Flavin-Bound GDH Derived from Mucor)

To a 0.5 L Sakaguchi flask, 0.1 L of preculture medium (2.0% yeast extract, 4% glucose, pH 6.0) was added. Into the flask, about 1 cm$^2$ each of a preculture of Mucor prainii NISL0103, Mucor javanicus NISL0111, or Mucor circinelloides f. circinelloides NISL0117 on a plate was inoculated, followed by shaking culture at 130 rpm and 30° C. for two days. This was used as a seed culture. Into 20 L of the above medium in a 30 L jar fermenter (two jar fermenters), 0.2 L each of the seed culture was inoculated, followed by culture at 200 rpm, 30° C., and 0.5 vvm for three days. After the completion of the culture, 40 L of culture medium was filtered through a filter cloth to collect cells. Subsequently, the obtained cells were suspended in 10 mM acetate buffer (pH 5.0).

The above cells suspension was sent to a Dyno-Mill (150 mL/min) and homogenized. The supernatant was collected by centrifugation at 6,000×g for 30 minutes. This supernatant was concentrated using a hollow fiber membrane AIP2013 (Asahi Kasei Chemicals) with 6,000 molecular weight cut off. The concentrated enzyme solution was gradually added to achieve 70% saturation of ammonium sulfate to precipitate excess proteins. This was allowed to stand overnight at 4° C., followed by centrifugation (200,000 xg, 60 minutes) to collect a supernatant.

The supernatant was subjected to a Toyopearl Butyl-650 (Tosoh) column (26φ×28.5 cm), pre-equilibrated with buffer A (10 mM acetate buffer, 2 M ammonium sulfate, pH 5.0), for elution by linear gradient from buffer A to B (10 mM acetate buffer, pH 5.0). The eluted active fraction was concentrated using a Centricon Plus-70 (Millipore), dialyzed using buffer C (10 mM acetate buffer, pH 4.5), and was subjected to an SP Sepharose FastFlow (GE Healthcare) column (26φ×28.5 cm) for elution by linear gradient from buffer C to D (10 mM acetate buffer, 200 mM potassium chloride, pH 4.5). The eluted active fraction was concentrated to obtain purified enzyme.

Hereinafter, regarding the purified enzymes, GDHs derived from Mucor prainii NISL0103, Mucor javanicus NISL0111, and Mucor circinelloides f. circinelloides NISL0117 are referred to as MpGDH, MjGDH, and McGDH, respectively.

EXAMPLE 3

(Investigation of the Enzymatic Properties of Flavin-Bound GDH Derived from Mucor)

The properties of the purified GDHs obtained in Example 2 were investigated.

(a) Measurement of Absorption Spectra

MpGDH, MjGDH, and McGDH were dialyzed using 10 mM acetate buffer (pH 5.0), followed by the measurement of absorption spectra at 250-800 nm using a spectrophotometer U-3010 (Hitachi High-Technologies Co., Ltd.). FIG. 1 shows the measurement results (FIGS. 1 (A), (B), and (C) show the absorption spectra of MpGDH, MjGDH, and McGDH, respectively.). All the GDHs showed two maximal peaks at around 340-350 and 420-430 nm wavelengths, strongly suggesting that the GDHs of the invention are flavin-bound proteins because these absorption spectra are specific to a flavin enzyme.

(b) Measurement of GOD Activity

MpGDH, MjGDH, and McGDH obtained in Example 2 and a commercial glucose oxidase derived from Aspergillus niger (GOD, biozyme laboratories) were used to measure GDH and GOD activities. Table 2 shows the results.

GDH activity was measured as described in Example 1. GOD activity was measured using 4-aminoantipyrine (4-AA) and N-ethyl-N-(2-hydroxy-3-sulfopropyl)-3-methylaniline (TOOS) as described below. To initiate a reaction, 30.0 mL of 100 mM phosphate buffer (pH 7.0), 6.0 mL of 833 mM D-glucose solution, 0.3 mL of 25 mM 4-AA solution, 0.3 mL of 40 mM TOOS solution, and 0.3 mL of 500 U/mL POD solution were mixed, of which 3.0 mL was transferred into a test tube and incubated at 37° C. for five minutes, and 0.1 mL of an enzyme sample solution was added. An increase in the absorbance at 555 nm ($\Delta A555$) per minute due to the progress of the enzyme reaction was determined to calculate GOD activity according to the following formula. At that time, one unit of the GOD activity is defined as the amount of an enzyme that generates 1 μmol of $H_2O_2$ at 37° C. within one minute in the presence of 131 mM D-glucose.

$$GOD\ activity\ (U/ml) = \frac{-(\Delta A555 - \Delta A555_{blank}) \times 3.1 \times df}{32.8 \times 0.5 \times 0.1 \times 1.0} \quad \text{[Formula 3]}$$

The formula indicates 3.1 as the liquid volume (mL) of reaction reagent plus enzyme reagent, 32.8 as millimolar extinction coefficient (cm$^2$/μmol) under the activity assay conditions, 0.5 as the number of quinoneimine dye molecules generated when one $H_2O_2$ molecule is reduced, 0.1 as the liquid volume (mL) of an enzyme solution, 1.0 as the optical path length (cm) of a cell, $\Delta A555_{blank}$ as an increase in the absorbance at 555 nm per minute when 10 mM acetate buffer, instead of an enzyme sample solution, is added to initiate a reaction, and df as a dilution factor.

TABLE 2

Comparison between the GDH and GOD activities of each enzyme

|  | GDH activity | GOD activity |
|---|---|---|
| MpGDH | 8.80 U/mL | 0.00 U/mL |
| MjGDH | 9.90 U/mL | 0.00 U/mL |
| McGDH | 9.42 U/mL | 0.00 U/mL |
| GOD derived from *Aspergillus niger* | 3.50 U/mL | 9.38 U/mL |

As shown in Table 2, MpGDH, MjGDH, and McGDH showed no GOD activity and showed exclusively GDH activity. On the other hand, GOD was demonstrated to show mainly GOD activity and simultaneously have GDH activity. Specifically, the GDH of the invention utilizes no oxygen as an electron acceptor and, therefore, is unlikely to be influenced by the dissolved oxygen of the reaction system in the measurement of D-glucose.

(c) Optimum pH

Figure 2:
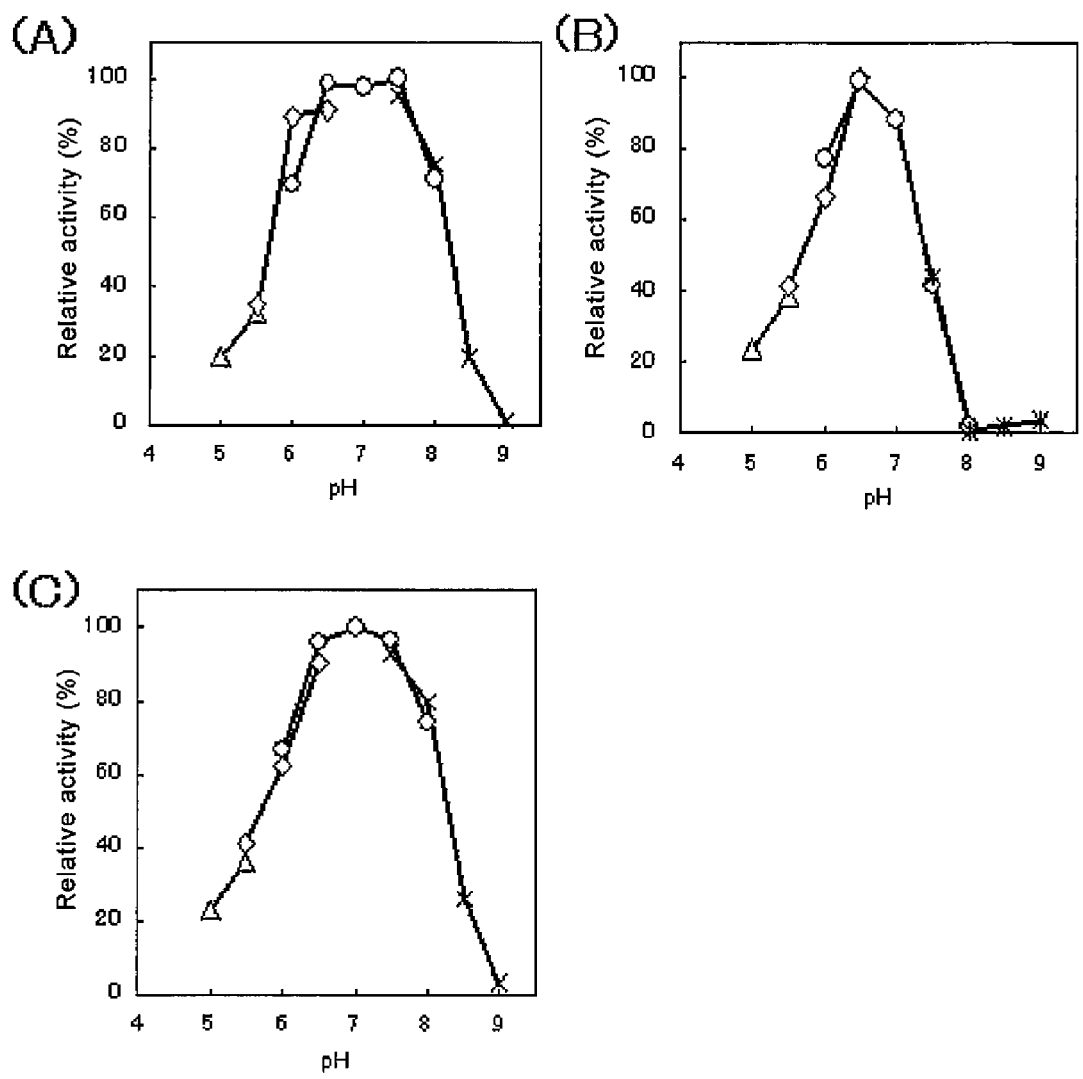
[FIG. 2] Optimum pH of any one of the flavin-bound GDHs used in the invention.

The optimum pH of the above flavin-bound GDH was investigated. FIG. 2 shows the results (FIGS. 2 (A), (B), and (C) show the results of MpGDH, MjGDH, and McGDH, respectively.). Specifically, 100 mM potassium acetate buffer (pH 5.0-5.5, plotted with triangle mark), 100 mM MES-NaOH buffer (pH 5.5-6.5, plotted with diamond mark), 100 mM potassium phosphate buffer (pH 6.0-8.0, plotted with circle mark), and 100 mM Tris-HCl buffer (pH 7.5-9.0, plotted with cross mark) were used to carry out enzyme reactions at 37° C. at each pH in order to compare relative activities.

As a result, all the above flavin-bound GDHs showed the highest activity at pH 6.5 or 7.0 and had optimum pH at around 7.0. Individually, MpGDH and McGDH showed the highest relative activity at pH 7.0 and 80% or above of the maximum relative activity at pH 6.5-7.5, allowing preferable use in this range. MjGDH showed the highest relative activity at pH 6.5 and 80% or above of the maximum relative activity at pH 6.0-7.0, allowing preferable use in this range.

(d) Optimum Temperature Range

Figure 3:
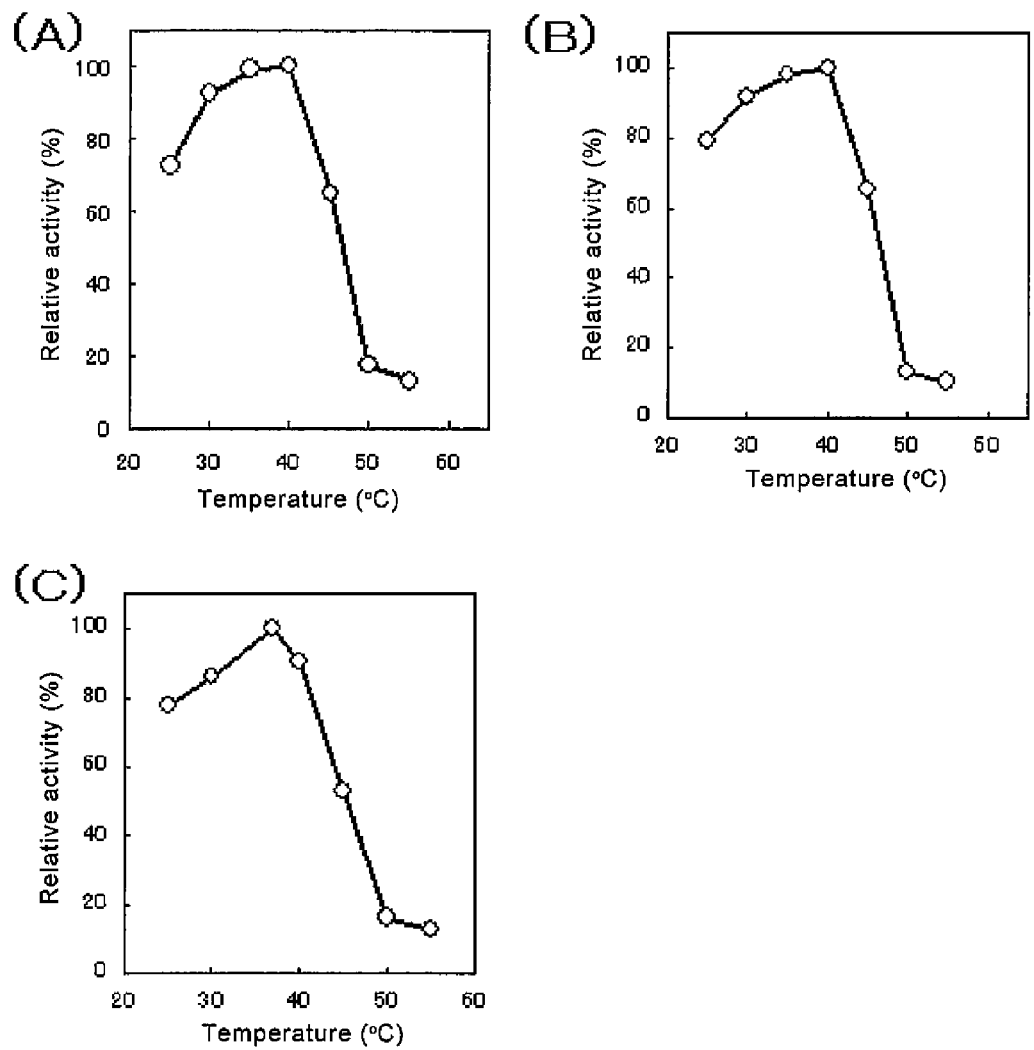
[FIG. 3] Optimum temperature of any one of the flavin-bound GDHs used in the invention.

The activity of the enzyme was measured at various temperatures according to the activity assay described in Example 1. Specifically, to initiate a reaction at each temperature, 1.79 mL of 100 mM phosphate buffer (pH 7.0), 0.08 mL of 1.25 M D-glucose solution, and 0.01 mL of 20 mM DCIP solution were mixed, followed by incubation at each temperature, instead of 37° C., for five minutes, and 0.02 mL of 20 mM PMS solution and 0.1 mL of an enzyme sample solution were added. Absorbance was measured at the initiation of the reaction and two minutes later to determine a decrease in the absorbance at 600 nm per minute due to the progress of the enzyme reaction. FIG. 3 shows the results (FIGS. 3 (A), (B), and (C) show the results of MpGDH, MjGDH, and McGDH, respectively.). All of them showed the maximum activity at around 37° C. The temperature range that showed 80% or above activity relative to the maximum one was 30-40° C. Thus, the optimum temperature range of the flavin-bound GDH of the invention was 30-40° C. The most preferable temperature was 37° C.

(e) Km Values for D-Glucose

In the above activity assay, activity was measured by changing the concentration of D-glucose as a substrate to determine the Michaelis constant (Kin) from a Lineweaver-Burk plot. As a result, the Km values for D-glucose were 31.1 mM for MpGDH, 26.4 mM for MjGDH, and 33.2 mM for McGDH.

(f) Thermal Stability

Figure 4:
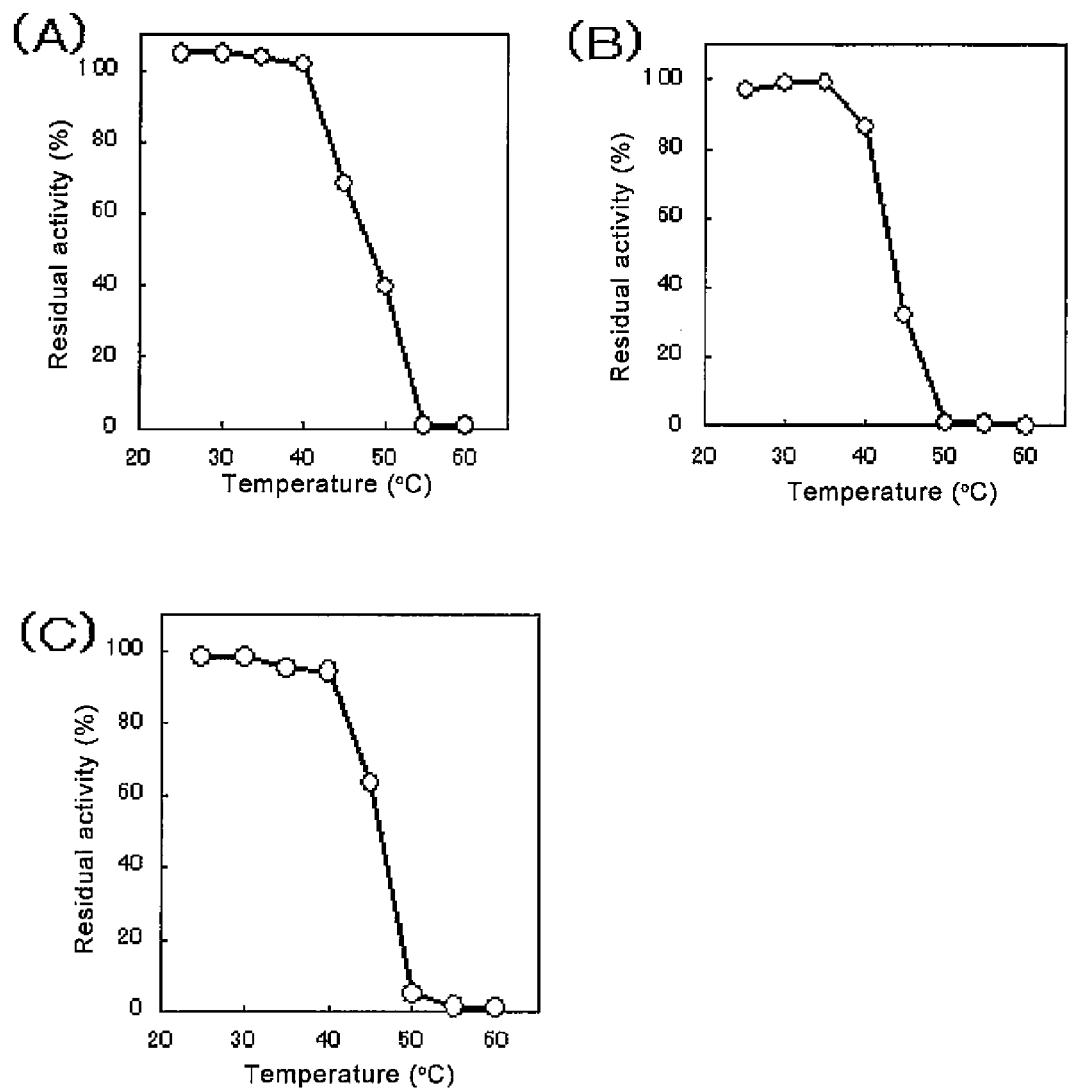
[FIG. 4] Thermal stability of any one of the flavin-bound GDHs used in the invention.

FIG. 4 shows the results of the thermal stability of the flavin-bound GDHs of the invention, treated with 100 mM potassium acetate buffer (pH 5.0) at each temperature for 15 minutes (FIGS. 4 (A), (B), and (C) show the results of MpGDH, MjGDH, and McGDH, respectively.). The flavin-bound GDHs of the invention had 80% or above residual activity after heat treatment at 40° C. for 15 minutes, demonstrating that they were stable up to about 40° C.

(g) Range of Stable pH

Figure 5:
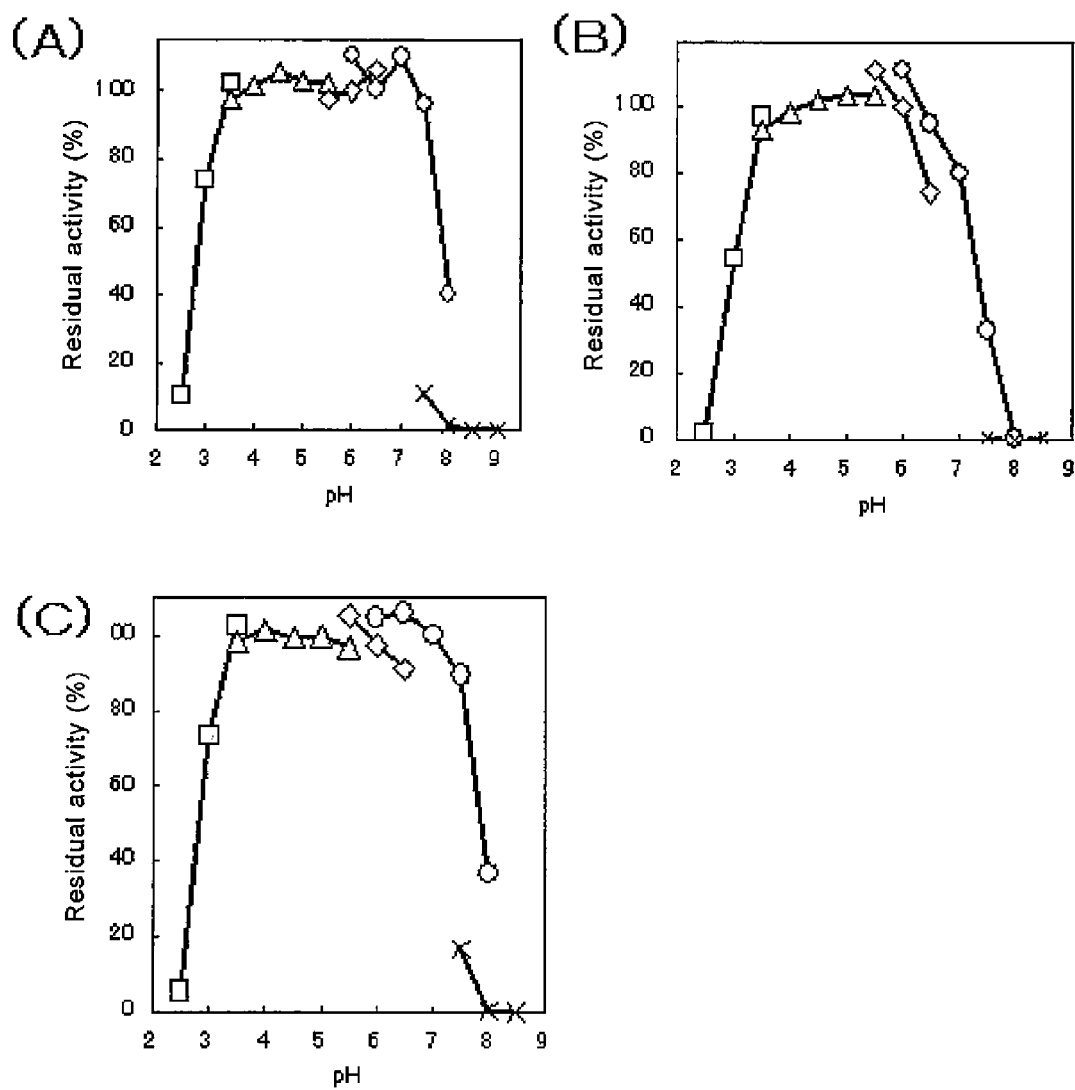
[FIG. 5] pH stability of any one of the flavin-bound GDHs used in the invention.

Subsequently, the stable pH of these flavin-bound GDHs was examined. FIG. 5 shows the results (FIGS. 5 (A), (B), and (C) show the results of MpGDH, MjGDH, and McGDH, respectively.). Specifically, 100 mM glycine-HCl buffer (pH 2.5-3.5, plotted with square mark), 100 mM potassium acetate buffer (pH 3.5-5.5, plotted with triangle mark), 100 mM MES-NaOH buffer (pH 5.5-6.5, plotted with diamond mark), 100 mM potassium phosphate buffer (pH 6.0-8.0, plotted with circle mark), and 100 mM Tris-HCl buffer (pH 7.5-9.0, plotted with cross mark) were used to carry out treatment at each pH and at 25° C. for 16 hours, followed by measurement of the residual activity of the flavin-bound GDH. As a result, the pH range that showed 80% or above activity relative to the activity at around pH 5.0 that showed maximum residual activity was pH 3.5-7.0. Thus, the stable pH range of these flavin-bound GDHs was demonstrated to be pH 3.5-7.0.

(h) Molecular Weight

Figure 6:
[FIG. 6] SDS-polyacrylamide gel electrophoresis of any one of the flavin-bound GDHs used in the invention.

The molecular weights of MpGDH, MjGDH, and McGDH were determined by SDS-polyacrylamide electrophoresis with SuperSep Ace 10-20% (Wako Pure Chemical Industries, Ltd.). Each flavin-bound GDH was deglycosylated using a deglycosylation kit (Enzymatic Deglycosylation Kit, PZM) and electrophoresed in the same manner. FIG. 6 shows the results. The electrophoresed samples are as follows:

Lane 1: Molecular weight marker (New England Biolabs, Inc., protein ladder (10-250 kDa), 250 kDa, 150 kDa, 100 kDa, 80 kDa, 60 kDa, 50 kDa, 40 kDa, 30 kDa, 25 kDa, 20 kDa, and 15 kDa from the top)
Lane 2: MpGDH
Lane 3: Deglycosylated MpGDH
Lane 4: MjGDH
Lane 5: Deglycosylated MjGDH
Lane 6: McGDH
Lane 7: Deglycosylated McGDH
Lane 8: Enzyme used for deglycosylation As shown in FIG. 6, the molecular weights of these flavin-bound GDHs are about 90-130 kDa for MpGDH, about 100-150 kDa for MjGDH, and about 130-200 kDa for McGDH. The molecular weight after deglycosylation using a deglycosylation kit (Enzymatic Deglycosylation Kit, PZM) was about 80 kDa for all of MpGDH, MjGDH, and McGDH.

(i) Substrate Specificity

According to the enzyme activity assay of Example 1, D-glucose, maltose, D-galactose, D-xylose, mannose, sucrose, trehalose, maltotriose, and maltotetraose were used as substrates to measure the activities of the flavin-bound GDHs for each substrate. Substrate specificity was determined to be 50 mM. Table 3 shows the results.

TABLE 3

Relative activities for the substrates of each GDH

| Substrate | Relative activity (%) | | | | |
|---|---|---|---|---|---|
| | MpGDH | MjGDH | McGDH | Patent document 2 GDH | Patent document 3 GDH |
| D-Glucose | 100 | 100 | 100 | 100 | 100 |
| Maltose | 1.09 | 0.72 | 1.25 | 1.4 | 0.00 |
| D-Galactose | 0.44 | 0.54 | 1.25 | 1.2 | — |
| D-Xylose | 1.53 | 1.43 | 2.00 | 9.1 | 17.6 |
| Mannose | 0.66 | 0.36 | 1.00 | 2.8 | 1.40 |
| Sucrose | 0.00 | 0.36 | 0.25 | 0.1> | — |
| Trehalose | 0.22 | 0.00 | 0.25 | 1.7 | — |
| Maltotriose | 0.88 | 0.54 | 1.00 | — | — |
| Maltotetraose | 0.66 | 0.54 | 1.50 | — | — |

As a result, these flavin-bound GDHs were demonstrated to have very low reactivity to each sugar compound, relative to 100% of the activity to D-glucose. Activities to maltose, D-galactose, D-xylose were all 2% or below.

(j) Inhibitory Effects of 1,10-Phenanthroline

The inhibitory effects of 1,10-phenanthroline on the activities of these flavin-bound GDHs were examined by the following method. According to the enzyme activity assay of Example 1, the enzyme activities when 1,10-phenanthroline was added at final concentrations of 1, 5, 10, 25, and 50 mM were determined to calculate the inhibitory rates relative to 0% of the inhibitory rate when no 1,10-phenanthroline was added. Table 4 shows the results.

TABLE 4

Inhibitory effects of 1,10-phenanthroline

| Final concentration of 1,10-phenanthroline (mM) | GDH inhibition rate (%) | | |
|---|---|---|---|
| | MpGDH | MjGDH | McGDH |
| 0 | 0 | 0 | 0 |
| 50 | 68.6 | 88.9 | 68.5 |
| 25 | 44.1 | 64.7 | 36.2 |
| 10 | 23.9 | 23.5 | 12.8 |
| 5 | 10.1 | 13.1 | 8.23 |
| 1 | 3.72 | 3.27 | 1.95 |

The inhibitory effects of 1,10-phenanthroline on the flavin-bound GDHs of the invention were as low as about 2-4% when 1,10-phenanthroline was added at 1 mM and about 10% even when 1,10-phenanthroline was added at 5 mM.

EXAMPLE 4

(Investigation 1 of the Quantitative Properties of Glucose Levels Using the Flavin-Bound) GDHs Derived from *Mucor*)

Glucose levels were measured using the above flavin-bound GDHs. Specifically, to initiate a reaction, 1.79 mL of 100 mM phosphate buffer (pH 7.0), 0.08 mL of D-glucose solution (250, 750, 1,250, 1,750, 2,500, 3,250, 4,000, and 5,000 mg/dL), and 0.01 mL of 20 mM DCIP solution were mixed, followed by incubation at 37° C. for five minutes, and 0.02 mL of 20 mM PMS solution and 0.1 mL of 0.8 U/mL GDH solution were added. The relationship between a decrease in the absorbance at 600 nm ($\Delta A600$) per minute due to the progress of the enzyme reaction and the final concentration of glucose is shown in FIG. 7 (FIGS. 7 (A), (B), and (C) show the measurement results of MpGDH, MjGDH, and McGDH, respectively.).

Figure 7:
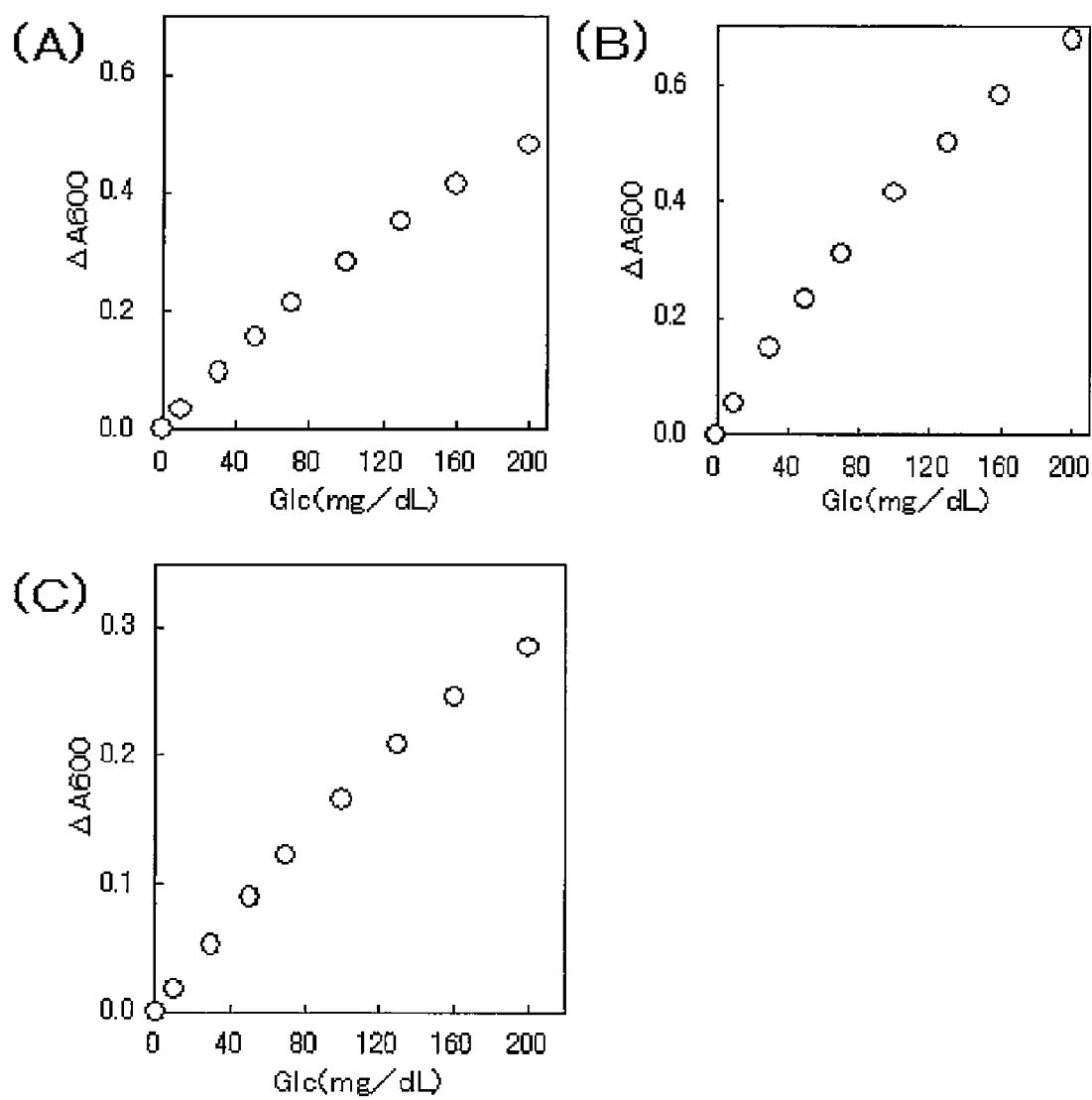
[FIG. 7] Measurement of D-glucose using any one of the flavin-bound GDHs used in the invention.

As shown in FIG. 7, it was demonstrated that glucose levels in measurement samples could be accurately measured at a final concentration of 200 mg/dL or below using the flavin-bound GDHs derived from *Mucor*.

EXAMPLE 5

(Investigation 2 of the Quantitative Properties of Glucose Levels Using the Flavin-Bound GDHs Derived from *Mucor*)

To initiate a reaction, 1.77 mL of 100 mM phosphate buffer (pH 7.0), 0.02 mL of D-glucose solution (10,000 and 16,000 mg/dL), and 0.01 mL of 20 mM DCIP solution were mixed, and, subsequently, 0.08 mL of maltose solution (3,000, 6,000, 9,000, 12,000, and 15,000 mg/dL), D-galactose solution (1,500, 3,000, 4,500, 6,000, and 7,500 mg/dL), or D-xylose solution (1,000, 2,000, 3,000, 4,000, and 5,000 mg/dL) was added, followed by incubation at 37° C. for five minutes, and 0.02 mL of 20 mM PMS solution and 0.1 mL of 2.0 U/mL GDH solution were added. The relationship between a decrease in the absorbance at 600 nm ($\Delta A600$) per minute due to the progress of the enzyme reaction and the final concentration of glucose is shown in Table 5-7.

TABLE 5

Comparison of glucose measurements in samples with the addition of various sugar compounds (Enzyme: MpGDH)

| D-Glucose concentration (mg/mL) | 100 | | | | | |
|---|---|---|---|---|---|---|
| Maltose concentration (mg/mL) | 0 | 120 | 240 | 360 | 480 | 600 |
| $\Delta A600$ | 0.394 | 0.393 | 0.398 | 0.398 | 0.399 | 0.401 |
| Relative value (%) | 100 | 100 | 101 | 101 | 101 | 102 |
| D-Glucose concentration (mg/mL) | 160 | | | | | |
| Maltose concentration (mg/mL) | 0 | 120 | 240 | 360 | 480 | 600 |
| $\Delta A600$ | 0.534 | 0.535 | 0.540 | 0.540 | 0.542 | 0.535 |
| Relative value (%) | 100 | 100 | 101 | 101 | 102 | 100 |
| D-Glucose concentration (mg/mL) | 100 | | | | | |
| D-Galactose concentration (mg/mL) | 0 | 60 | 120 | 180 | 240 | 300 |
| $\Delta A600$ | 0.394 | 0.392 | 0.393 | 0.393 | 0.393 | 0.394 |
| Relative value (%) | 100 | 100 | 100 | 100 | 100 | 100 |
| D-Glucose concentration (mg/mL) | 160 | | | | | |
| D-Galactose concentration (mg/mL) | 0 | 60 | 120 | 180 | 240 | 300 |
| $\Delta A600$ | 0.534 | 0.513 | 0.530 | 0.535 | 0.529 | 0.533 |
| Relative value (%) | 100 | 96 | 99 | 100 | 99 | 100 |
| D-Galactose concentration (mg/mL) | 100 | | | | | |
| D-Xylose concentration (mg/mL) | 0 | 40 | 80 | 120 | 160 | 200 |

TABLE 5-continued

Comparison of glucose measurements in samples with the addition of various sugar compounds (Enzyme: MpGDH)

| | | | | | | |
|---|---|---|---|---|---|---|
| ΔA600 | 0.394 | 0.388 | 0.390 | 0.389 | 0.386 | 0.386 |
| Relative value (%) | 100 | 100 | 99 | 99 | 98 | 98 |
| D-Glucose concentration (mg/mL) | | | 160 | | | |
| D-Xylose concentration (mg/mL) | 0 | 40 | 80 | 120 | 160 | 200 |
| ΔA600 | 0.534 | 0.530 | 0.529 | 0.525 | 0.527 | 0.522 |
| Relative value (%) | 100 | 99 | 99 | 98 | 99 | 98 |

TABLE 6

Comparison of glucose measurements in samples with the addition of various sugar compounds (Enzyme: MjGDH)

| | | | | | | |
|---|---|---|---|---|---|---|
| D-Glucose concentration (mg/mL) | | | 100 | | | |
| Maltose concentration (mg/mL) | 0 | 120 | 240 | 360 | 480 | 600 |
| ΔA600 | 0.857 | 0.861 | 0.867 | 0.864 | 0.871 | 0.868 |
| Relative value (%) | 100 | 101 | 101 | 101 | 102 | 101 |
| D-Glucose concentration (mg/mL) | | | 160 | | | |
| Maltose concentration (mg/mL) | 0 | 120 | 240 | 360 | 480 | 600 |
| ΔA600 | 1.222 | 1.230 | 1.222 | 1.234 | 1.228 | 1.238 |
| Relative value (%) | 100 | 101 | 100 | 101 | 101 | 101 |
| D-Glucose concentration (mg/mL) | | | 100 | | | |
| D-Galactose concentration (mg/mL) | 0 | 60 | 120 | 180 | 240 | 300 |
| ΔA600 | 0.857 | 0.863 | 0.864 | 0.865 | 0.863 | 0.854 |
| Relative value (%) | 100 | 101 | 101 | 101 | 101 | 100 |
| D-Glucose concentration (mg/mL) | | | 160 | | | |
| D-Galactose concentration (mg/mL) | 0 | 60 | 120 | 180 | 240 | 300 |
| ΔA600 | 1.222 | 1.226 | 1.222 | 1.224 | 1.216 | 1.214 |
| Relative value (%) | 100 | 100 | 100 | 100 | 100 | 99 |
| D-Glucose concentration (mg/mL) | | | 100 | | | |
| D-Xylose concentration (mg/mL) | 0 | 40 | 80 | 120 | 160 | 200 |
| ΔA600 | 0.857 | 0.869 | 0.851 | 0.847 | 0.857 | 0.856 |
| Relative value (%) | 100 | 101 | 99 | 100 | 100 | 100 |
| D-Glucose concentration (mg/mL) | | | 160 | | | |
| D-Xylose concentration (mg/mL) | 0 | 40 | 80 | 120 | 160 | 200 |
| ΔA600 | 1.222 | 1.234 | 1.212 | 1.222 | 1.212 | 1.218 |
| Relative value (%) | 100 | 101 | 99 | 100 | 99 | 100 |

TABLE 7

Comparison of glucose measurements in samples with the addition of various sugar compounds (Enzyme: McGDH)

| | | | | | | |
|---|---|---|---|---|---|---|
| D-Glucose concentration (mg/mL) | | | 100 | | | |
| Maltose concentration (mg/mL) | 0 | 120 | 240 | 360 | 480 | 600 |
| ΔA600 | 0.431 | 0.434 | 0.443 | 0.444 | 0.443 | 0.444 |
| Relative value (%) | 100 | 101 | 103 | 103 | 103 | 103 |
| D-Glucose concentration (mg/mL) | | | 160 | | | |
| Maltose concentration (mg/mL) | 0 | 120 | 240 | 360 | 480 | 600 |
| ΔA600 | 0.637 | 0.646 | 0.649 | 0.654 | 0.652 | 0.653 |
| Relative value (%) | 100 | 101 | 102 | 103 | 102 | 103 |
| D-Glucose concentration (mg/mL) | | | 100 | | | |
| D-Galactose concentration (mg/mL) | 0 | 60 | 120 | 180 | 240 | 300 |

TABLE 7-continued

Comparison of glucose measurements in samples with the addition of various sugar compounds (Enzyme: McGDH)

| ΔA600 | 0.431 | 0.437 | 0.438 | 0.439 | 0.443 | 0.441 |
|---|---|---|---|---|---|---|
| Relative value (%) | 100 | 101 | 102 | 102 | 103 | 102 |
| D-Glucose concentration (mg/mL) | | | 160 | | | |
| D-Galactose concentration (mg/mL) | 0 | 60 | 120 | 180 | 240 | 300 |
| ΔA600 | 0.637 | 0.644 | 0.646 | 0.639 | 0.645 | 0.640 |
| Relative value (%) | 100 | 101 | 101 | 100 | 101 | 101 |
| D-Glucose concentration (mg/mL) | | | 100 | | | |
| D-Xylose concentration (mg/mL) | 0 | 40 | 80 | 120 | 160 | 200 |
| ΔA600 | 0.431 | 0.439 | 0.440 | 0.443 | 0.442 | 0.435 |
| Relative value (%) | 100 | 102 | 102 | 103 | 103 | 101 |
| D-Glucose concentration (mg/mL) | | | 160 | | | |
| D-Xylose concentration (mg/mL) | 0 | 40 | 80 | 120 | 160 | 200 |
| ΔA600 | 0.637 | 0.644 | 0.645 | 0.643 | 0.646 | 0.642 |
| Relative value (%) | 100 | 101 | 101 | 101 | 101 | 101 |

As shown in Tables 5-7, it was demonstrated that glucose levels in samples containing maltose at a final concentration of 600 mg/dL or below, D-galactose at a final concentration of 300 mg/dL or below, or D-xylose at a final concentration of 200 mg/dL or below could be accurately measured using these flavin-bound GDHs derived from *Mucor*.

EXAMPLE 6

(Investigation 3 of the Quantitative Properties of Glucose Levels Using the Flavin-Bound GDHs)

To initiate a reaction, 1.61 mL of 100 mM phosphate buffer (pH 7.0), 0.02 mL of D-glucose solution (10,000 and 16,000 mg/dL), and 0.01 mL of 20 mM DCIP solution were mixed, and, subsequently, 0.08 mL each of maltose solution (3,000, 6,000, 9,000, 12,000, and 15,000 mg/dL), D-galactose solution (1,500, 3,000, 4,500, 6,000, and 7,500 mg/dL), and D-xylose solution (1,000, 2,000, 3,000, 4,000, and 5,000 mg/dL) was added, followed by incubation at 37° C. for five minutes, and 0.02 mL of 20 mM PMS solution and 0.1 mL of 2.0 U/mL flavin-bound GDH solution were added. The relationship between a decrease in the absorbance at 600 nm (ΔA600) per minute due to the progress of the enzyme reaction and the final concentration of glucose is shown in Tables 8-9.

TABLE 8

Comparison of glucose measurements in samples with the addition of three kinds of sugar compounds (Enzyme: MpGDH)

| D-Glucose concentration (mg/mL) | | | 100 | | | |
|---|---|---|---|---|---|---|
| Maltose concentration (mg/mL) | 0 | 120 | 240 | 360 | 480 | 600 |
| D-Galactose concentration (mg/mL) | 0 | 60 | 120 | 180 | 240 | 300 |
| D-Xylose concentration (mg/mL) | 0 | 40 | 80 | 120 | 160 | 200 |

TABLE 8-continued

Comparison of glucose measurements in samples with the addition of three kinds of sugar compounds (Enzyme: MpGDH)

| ΔA600 | 0.637 | 0.640 | 0.644 | 0.650 | 0.652 | 0.647 |
|---|---|---|---|---|---|---|
| Relative value (%) | 100 | 101 | 101 | 102 | 102 | 102 |
| D-Glucose concentration (mg/mL) | | | 160 | | | |
| Maltose concentration (mg/mL) | 0 | 120 | 240 | 360 | 480 | 600 |
| D-Galactose concentration (mg/mL) | 0 | 60 | 120 | 180 | 240 | 300 |
| D-Xylose concentration (mg/mL) | 0 | 40 | 80 | 120 | 160 | 200 |
| ΔA600 | 0.726 | 0.747 | 0.750 | 0.750 | 0.748 | 0.755 |
| Relative value (%) | 100 | 103 | 103 | 103 | 103 | 104 |

TABLE 9

Comparison of glucose measurements in samples with the addition of three kinds of sugar compounds (Enzyme: MjGDH)

| D-Glucose concentration (mg/mL) | | | 100 | | | |
|---|---|---|---|---|---|---|
| Maltose concentration (mg/mL) | 0 | 120 | 240 | 360 | 480 | 600 |
| D-Galactose concentration (mg/mL) | 0 | 60 | 120 | 180 | 240 | 300 |
| D-Xylose concentration (mg/mL) | 0 | 40 | 80 | 120 | 160 | 200 |
| ΔA600 | 0.746 | 0.722 | 0.728 | 0.734 | 0.725 | 0.734 |
| Relative value (%) | 100 | 97 | 98 | 98 | 97 | 98 |
| D-Glucose concentration (mg/mL) | | | 160 | | | |
| Maltose concentration (mg/mL) | 0 | 120 | 240 | 360 | 480 | 600 |
| D-Galactose concentration (mg/mL) | 0 | 60 | 120 | 180 | 240 | 300 |
| D-Xylose concentration (mg/mL) | 0 | 40 | 80 | 120 | 160 | 200 |
| ΔA600 | 1.076 | 1.049 | 1.052 | 1.058 | 1.067 | 1.070 |
| Relative value (%) | 100 | 97 | 98 | 98 | 99 | 99 |

Tables 8-9 demonstrate that MpGDH or MjGDH allows extremely accurate measurement of glucose levels in samples containing maltose at a final concentration of 600 mg/dL or below, D-galactose at a final concentration of 300 mg/dL or below, or D-xylose at a final concentration of 200 mg/dL or below.

EXAMPLE 7

(Cloning of a Flavin-Bound GDH Gene Derived from *Mucor* and Preparation of the *E. coli* Transformant)

(1) mRNA Preparation

*Mucor prainii* NISL0103 was inoculated into 3 mL of malt extract medium (2.0% malt extract, 4.0% glucose, 0.1% polypeptone, pH 6.0), followed by shaking culture at 30° C. for two days. This culture medium was filtered through a filter paper to collect mycelia. The obtained mycelia were frozen in liquid nitrogen and homogenized using a mortar. Subsequently, mRNA was obtained from the homogenized mycelia using ISOGEN (Nippon Gene) according to the protocol of the kit.

(2) Determination of the Partial Amino Acid Sequence of GDH

The MpGDH obtained in Example 2 was subjected to SuperSep Ace 10-20% (Wako Pure Chemical Industries, Ltd.) and electrophoresed. The electrophoresed gel was stained using Quick-CBB (Wako Pure Chemical Industries, Ltd.). A band portion corresponding to the molecular weight of the enzyme was excised. The excised gel was outsourced to an outside agency to obtain the internal amino acid sequence information of the protein contained in the gel. The resulting amino acid sequences were LVENFTPPTPAQIE (SEQ ID NO: 5) and IRNSTDEWANYY (SEQ ID NO: 6).

(3) Determination of the GDH Gene Sequences

Degenerate primers containing mixed bases (exemplary primers are shown in SEQ ID NO: 7 (forward primer) and SEQ ID NO: 8 (reverse primer)) were prepared based on the above partial amino acid sequence information. In the single character codes of SEQ ID NO: 7 and 8, mixed bases are represented as h=a+c+t, r=a+g, y=c+t, and d=a+g+t. The mRNA of *Mucor prainii* NISL0103, prepared in the above (1), was used as a template to conduct RT-PCR using Prime-Script RT-PCR Kit (Takara Bio) according to the protocol of the kit. The oligo dT primer supplied with the kit was used for reverse transcription reaction. The degenerate primers of SEQ ID NO: 7 and 8 were used for cDNA amplification by PCR. The reaction solution was subjected to agarose gel electrophoresis. A single band corresponding to about 800-bp length was detected. The amplified DNA fragment contained in this band was purified and ligated to pT7Blue (Novagen) using Ligation Convenient Kit (Nippon Gene), constructing a recombinant plasmid, pTMGD-1.

Subsequently, the resulting pTMGD-1 was used to transform *E. coli* JM109 competent cells (Nippon Gene) by known heat shock method. Plasmids were extracted and purified from the resulting *E. coli* transformant using GenElute Plasmid. Miniprep Kit (Sigma) to determine the base sequence of the amplified DNA fragment (767 bp) contained in the plasmids.

Based on the sequence information of the resulting amplified DNA fragment, the unknown 3' and 5' regions of the GDH gene were determined using 3'- and 5'-Full RACE Core Sets (Takara Bio), respectively. The 3-site adaptor-primer supplied with the kit was used for 3'-Full RACE Core Set, while the primers of SEQ ID NO: 10, 11, 12, 13, and 14 were used for 5'-Full RACE Core Set, according to the protocols of the kits. The base sequences of the DNA fragments contained in the multiple plasmids obtained according to the above method were determined, revealing a GDH gene sequence with an entire length of 1,926 bp, derived from *Mucor prainii* NISL0103, as shown in SEQ ID NO: 2 and 4. The amino acid sequences of the enzyme gene, predicted from the gene sequences, are shown in SEQ ID NO: 1 and 3.

(4) *E. Coli* Transformation and Detection of GDH Activity

N-terminal (SEQ ID NO: 15) and C-terminal (SEQ ID NO: 16) region primers were prepared. These primers and the mRNA of *Mucor prainii* NISL0103, prepared in the above (1), were used to conduct RT-PCR.

The reaction solution was subjected to agarose gel electrophoresis. A single band corresponding to about 2-kbp length was detected. The amplified DNA fragment contained in this band was purified and ligated to pUC19 (Takara Bio), digested with restriction enzyme SmaI, constructing a recombinant plasmid, puc-MGD.

The resulting recombinant plasmid, puc-MGD, was used to transform *E. coli* JM109 competent cells (Nippon Gene) by known heat shock method. Subsequently, the transformed *E. coli* JM109 (puc-MGD) bacteria were shaking cultured at 37° C. for two hours in 10 mL of TY medium (1% Bacto-tryptone, 0.5% Bacto-yeast extract, 0.5% NaCl, pH 7.0), supplemented with 100 µg/mL ampicillin and 1 mM IPTG at final concentrations, followed by shaking culture at 30° C. for six hours.

This culture medium was cooled on ice and homogenized using an ultrasonic disintegrator (Ultrasonicgenerator, Nissei) for 20 seconds four times. The homogenized solution was added into an Eppendorf tube, followed by centrifugation using a microcentrifuge at 12,000 rpm for 10 minutes. The supernatant fraction was transferred into another Eppendorf tube to be used as a crude enzyme solution. The GDH activity in this crude enzyme solution was measured according to the above activity assay, demonstrating the enzyme activity of the flavin-bound GDH of the invention.

(5) Introduction of the Flavin-Bound GDH Gene Derived from *Mucor*, with its N-Terminal Sequence Deleted, into *E. Coli* and Confirmation of GDH Activity To obtain a DNA fragment encoding a GDH derived from *Mucor*, suitable for recombinant expression in *E. coli*, a gene sequence with its codon usage adjusted for *E. coli*, was designed, and the entire gene was synthesized. The entire DNA sequence synthesized is shown in SEQ ID NO: 17. The synthesized DNA was used as a template. N-terminal (SEQ ID NO: 18) and C-terminal (SEQ ID NO: 21) region primers were prepared for insertion into the NdeI-BamHI site of pET-22b (+) vector (Novagen) by In-Fusion method (Clontech), constructing a recombinant plasmid (pET-22b-MpFull).

This recombinant plasmid was introduced into *E. coli* BL21 (DE3) competent cells (Nippon Gene) by known heat shock method. Plasmids were extracted according to a routine method. The DNA sequence of the full-length GDH gene derived from *Mucor* corresponded to SEQ ID NO: 17. The amino acid residues predicted from the cDNA sequence was 641 amino acids (SEQ ID NO: 3).

Subsequently, the above full-length sequence of the GDH derived from *Mucor* was analyzed using a signal peptide prediction program on the web (SignalP, www.ebs.dtu.dk/services/SignalP-2.0/), suggesting that a signal peptide may be cleaved between the 20th Ala and 21st Gln from the N terminus in the GDH (FIG. 8). Thus, it was assumed that deleting the N-terminal sequence to the 20th Ala might improve enzyme productivity in *E. coli*. Hence, a gene encoding a GDH with a deletion to the 20th Ala and Met added to the 21st Gln (referred to as NS1) was obtained as described below. In addition, a gene encoding a GDH with a deletion to the 20th Ala and the 21st Gln substituted by Met (referred to as NS2) was obtained in the same manner (FIG. 9).

First, the NS1 was cloned by In-Fusion using the combination of the oligonucleotide of SEQ ID NO: 19 as an N-terminal primer and a primer of SEQ ID NO: 21. Subsequently, a recombinant plasmid having a DNA sequence encoding the NS1 (pET-22b-MpNS1) was constructed in the same manner as for the above pET-22b-MpFull. This plasmid was introduced into *E. coli* BL21 (DE3) competent cells (Nippon Gene) by known heat shock method to obtain the *E. coli* transformant of the invention.

Subsequently, a recombinant plasmid having a DNA sequence encoding the NS2 (pET-22b-MpNS2) was constructed in the same manner by PCR using the combination of the oligonucleotide of SEQ ID NO: 20 as an N-terminal primer and a primer of SEQ ID NO: 21, and an *E. coli* transformant was obtained. Plasmids having the DNA sequences of the modified flavin-bound GDHs were examined for sequence errors by DNA sequencing. SEQ ID NO: 22 shows a DNA sequence encoding the above signal peptide-deleted mutant NS1. SEQ ID NO: 23 shows the corresponding amino acid sequence. SEQ ID NO: 24 shows a DNA sequence encoding the above signal peptide-deleted mutant NS2. SEQ ID NO: 25 shows the corresponding amino acid sequence.

E. coli strains, BL21 (DE3)/pET-22b-MpFull, BL21 (DE3)/pET-22b-MpNS1, and BL21 (DE3)/pET-22b-MpNS2, transformed with the recombinant plasmids obtained as described above (pET-22b-MpFull, pET-22b-MpNS1, and pET-22b-MpNS2, respectively), were inoculated into 10 mL of TY medium (1% Bacto-tryptone, 0.5% Bacto-yeast extract, 0.5% NaCl, pH 7.0) containing 100 µg/mL ampicillin and 1 mM IPTG and shaking cultured at 37° C. for four hours, followed by additional shaking culture at 20° C. overnight.

This culture medium was cooled on ice and homogenized using an ultrasonic disintegrator (Ultrasonicgenerator, Nissei) for 10 seconds once. The homogenized solution was added into an Eppendorf tube, followed by centrifugation using a microcentrifuge at 12,000 rpm for 10 minutes. The supernatant fraction was transferred into another Eppendorf tube to be used as a crude enzyme solution. The GDH activity in the resulting crude enzyme solution was measured according to the above activity assay and compared with that in 1 mL of culture medium, demonstrating that the enzyme activity of the E. coli transformant BL21 (DE3)/pET-22b-MpFull, into which a wild-type full-length GDH gene was introduced, was as low as 0.0815 U/ml. On the other hand, the activity of E. coli transformant BL21 (DE3)/pET-22b-MpNS1, into which a modified GDH gene with the N-terminal MKITAAIITVATAFASFASA (SEQ ID NO:33) deleted and M added was introduced, was 4.10 U/ml, while that of E. coli transformant BL21 (DE3)/pET-22b-MpNS2, into which a modified GDH gene with the N-terminal MKITAAIITVATAFASFASA (SEQ ID NO:33) deleted and the 21st Q substituted by M was introduced, was 3.43 U/ml. Specifically, the GDH productivity of E. coli transformants with the N terminus deleted at the specific lengths (BL21 (DE3)/pET-22b-MpNS1 and BL21 (DE3)/pET-22b-MpNS2) was demonstrated to be increased about 42-50 fold by deleting the amino acid sequence of the predicted signal peptide.

Specifically, the use of the E. coli transformant of the invention allows efficient production of the GDHs of the invention, which is of practical use, in smaller facilities. Furthermore, the culture process of these microorganisms of origin (i.e., Mucor), from which GDH is derived, included long-term culture (3-5 days), cells homogenization after collecting cells by centrifugation (enzyme extraction), and subsequent preparation of a crude enzyme solution through second centrifugation. However, the use of the E. coli transformant of the invention significantly shortens the culture time and reduces the burden of bacterial homogenization (enzyme extraction) because of the use of E. coli as a host, resulting in efficient GDH production.

FIG. 8 demonstrated that the signal peptide might be cleaved at around the 27th Ser from the N terminus, at which cleavage site score (C, Y) is slightly high. Thus, a GDH lacking MKITAAIITVATAFASFASAQQDTNSS (SEQ ID NO:35) was expressed in E. coli. First, a gene encoding a GDH with a deletion to the 27th Ser and Met added to the 28st Ser (referred to as NS3) was obtained as described below. In addition, a gene encoding a GDH with a deletion to the 27th Ser and the 28st Ser substituted by Met (referred to as NS4) was obtained in the same manner (FIG. 9).

The following peptides are identified in FIG. 9:

```
MpFull
                                         (SEQ ID NO: 37)
MKITAAIITVATAFASFASAQQDTNSSSTDTYDYVIVGGGVAGLALASRI

SENKDVTVAV

MpNS1
                                         (SEQ ID NO: 38)
MQQDTNSSSTDTYDYVIVGGGVAGLALASRISENKDVTVAV

MpNS2
                                         (SEQ ID NO: 39)
MQDTNSSSTDTYDYVIVGGGVAGLALASRISENKDVTVAV

MpNS3
                                         (SEQ ID NO: 40)
MSTDTYDYVIVGGGVAGLALASRISENKDVTVAV

MpNS4
                                         (SEQ ID NO: 41)
MTDTYDYVIVGGGVAGLALASRISENKDVTVAV
```

First, PCR was conducted for NS3 using the combination of the primers of SEQ ID NO: 26 and 27 and pET-22b-MpFull as a template. The resulting PCR-amplified fragment was digested with NdeI. The reaction solution was subjected to agarose gel electrophoresis. A single band corresponding to about 7,400-bp length was detected. The amplified DNA fragment contained in this band was purified and ligated using Ligation Convenient Kit (Nippon Gene), constructing a recombinant plasmid (pET-22b-MpNS3) having a DNA sequence encoding NS3. Subsequently, this plasmid was introduced into E. coli BL21 (DE3) competent cells (Nippon Gene) by heat shock method to obtain the E. coli transformant of the invention.

Subsequently, PCR was similarly conducted for NS4 using the combination of the primers of SEQ ID NO: 28 and 27 and pET-22b-MpFull as a template. A recombinant plasmid having a DNA sequence encoding the NS4 (pET-22b-MpNS4) was constructed in the same manner as for pET-22b-MpNS3, and an E. coli transformant was obtained. Plasmids having the DNA sequences of the modified flavin-bound GDHs were examined for sequence errors by DNA sequencing.

SEQ ID NO: 29 shows a DNA sequence encoding the above signal peptide-deleted mutant NS3. SEQ ID NO: 30 shows the corresponding amino acid sequence. SEQ ID NO: 31 shows a DNA sequence encoding the above signal peptide-deleted mutant NS4. SEQ ID NO: 32 shows the corresponding amino acid sequence.

E. coli strains, BL21 (DE3)/pET-22b-MpFull, BL21 (DE3)/pET-22b-MpNS3, and BL21 (DE3)/pET-22b-MpNS4, transformed with the recombinant plasmids obtained as described above (pET-22b-MpFull, pET-22b-MpNS3, and pET-22b-MpNS4, respectively), were inoculated into 2 mL of TY medium (1% Bacto-tryptone, 0.5% Bacto-yeast extract, 0.5% NaCl, pH 7.0) containing 100 µg/mL ampicillin and 1 mM IPTG and shaking cultured at 37° C. for three hours, followed by additional shaking culture at 20° C. overnight.

This culture medium was cooled on ice and homogenized using an ultrasonic disintegrator (Ultrasonicgenerator, Nissei) for 10 seconds once. The homogenized solution was added into an Eppendorf tube, followed by centrifugation using a microcentrifuge at 12,000 rpm for 10 minutes. The supernatant fraction was transferred into another Eppendorf tube to be used as a crude enzyme solution. The GDH activity in the resulting crude enzyme solution was measured according to the above enzyme activity assay and compared with that in 1 mL of culture medium, demonstrating that the activity of the *E. coli* transformant BL21 (DE3)/pET-22b-MpFull, into which a wild-type full-length GDH gene was introduced, was as low as 0.0196 U/ml. On the other hand, the activity of *E. coli* transformant BL21 (DE3)/pET-22b-MpNS3, into which a modified GDH gene with the N-terminal MKITAAI-ITVATAFASFASAQQDTNSS (SEQ ID NO:35) deleted and M added was introduced, was 0.0644 U/ml, while that of *E. coli* transformant BL21 (DE3)/pET-22b-MpNS4, into which a modified GDH gene with the N-terminal MKITAAIIT-VATAFASFASAQQDTNSS (SEQ ID NO:35) deleted and the 28st S substituted by M was introduced, was 0.0681 U/ml. Specifically, the GDH productivity of *E. coli* transformants with the N terminus deleted at the specific lengths (BL21 (DE3)/pET-22b-MpNS3 and BL21 (DE3)/pET-22b-MpNS4) was demonstrated to be increased about 3.3-3.5 fold by deleting the amino acid sequence of the predicted signal peptide.

The substrate specificity of the GDHs (NS1, NS2, NS3, and NS4) of the invention, produced by the *E. coli* transformant of the invention, was examined according to Examples 3 and 5, demonstrating that it was almost comparable with that of the purified GDH obtained in Example 2.

Industrial Applicability

An FAD-GDH that is less susceptible to the effects of dissolved oxygen and allows accurate measurement of glucose even in the presence of sugar compounds other than glucose in a sample can be efficiently produced.

[Sequence Listing]

Sequences

---

The invention claimed is:

1. A flavin-bound glucose dehydrogenase lacking the N-terminal region, comprising an amino acid sequence of MKITAAIITVATAFASFASA (SEQ ID NO:33) that exists in the N-terminal region from the amino acid sequence of the flavin-bound glucose dehydrogenase consisting of the amino acid sequence of SEQ ID NO: 1 or SEQ ID NO: 3, and having at least 85% sequence identity to said amino acid sequence of SEQ ID NO: 1 or SEQ ID NO:3.

* * * * *